(12) United States Patent
Van Breusegem et al.

(10) Patent No.: US 9,422,573 B2
(45) Date of Patent: Aug. 23, 2016

(54) METHODS AND MEANS FOR GENERATING MICROBIAL DISEASE RESISTANT PLANTS

(75) Inventors: Frank Van Breusegem, Ledeberg (BE); Annelies Inze, Niuwerkerken (BE); Janick Mathys, Heverlee (BE); Bruno Cammue, Alsemberg (BE)

(73) Assignees: VIB VZW, Ghent (BE); Universiteit Gent, Ghent (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 156 days.

(21) Appl. No.: 14/116,323

(22) PCT Filed: May 9, 2012

(86) PCT No.: PCT/EP2012/058513
§ 371 (c)(1),
(2), (4) Date: Jan. 13, 2014

(87) PCT Pub. No.: WO2012/152816
PCT Pub. Date: Nov. 15, 2012

(65) Prior Publication Data
US 2014/0325703 A1   Oct. 30, 2014

Related U.S. Application Data

(60) Provisional application No. 61/518,832, filed on May 11, 2011.

(51) Int. Cl.
| | |
|---|---|
| *C07K 14/41* | (2006.01) |
| *C12N 15/82* | (2006.01) |
| *C07K 14/415* | (2006.01) |
| *A01N 37/46* | (2006.01) |

(52) U.S. Cl.
CPC ............ *C12N 15/8282* (2013.01); *A01N 37/46* (2013.01); *C07K 14/415* (2013.01); *C12N 15/8281* (2013.01)

(58) Field of Classification Search
None
See application file for complete search history.

(56) References Cited

FOREIGN PATENT DOCUMENTS

| | | |
|---|---|---|
| EP | 1198985 | 4/2002 |
| WO | WO 2012/152816 A1 | 11/2012 |

OTHER PUBLICATIONS

Friedberg (Automated protein function prediction—the genomic challenge. Brief. Bioinformatics. 7: 225-242, 2006).*
Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
Tabata et al (The Kazusa DNA Research Institute, The Cold Spring Harbor and Washington University in St Louis Sequencing Consortium & The European Union Arabidopsis Genome Sequencing Consortium. Sequence and analysis of chromosome 5 of the plant Arabidopsis thaliana. Nature, 408: 823-826, 12. 14. 2000).*
Database EMBL, Apr. 14, 2005, XP002682995 retrieved from EBI accession No. AB016877.
Database UniProt, Aug. 10, 2010, XP002682996 retrieved from EBI accession No. D7M148.
Database UniProt, Aug. 10, 2010, XP002682997 retrieved from EBI accession No. D7M150.
Renata et al., The Arabidopsis thaliana Transcriptome in Response to Agrobacterium tumefaciens, Molecular Plant-Microbe Interactions, Jun. 1, 2006, pp. 665-681, vol. 19, No. 6.
Keykhoscrow et al., Application of antimicrobial peptides in agriculture and food industry, World Journal of Microbiology and Biotechnology, Feb. 19, 2009, pp. 933-944, vol. 25, No. 6, Kluwer Academic Publishers, DO.
PCT International Search Report, PCT/ep2012/058513, dated Sep. 21, 2012.
Definition of Gene, dated Nov. 3, 2015, at http://medical dictionary.thefreedictionary.com/chimeric+gene.

* cited by examiner

*Primary Examiner* — Medina A Ibrahim
*Assistant Examiner* — Wayne Zhong
(74) *Attorney, Agent, or Firm* — TraskBritt P.C.

(57) ABSTRACT

Described are genes and chimeric genes encoding anti-microbial peptides. These genes can be used to generate transgenic plants with an improved resistance to, for example, plant pathogenic fungi. Alternatively, the peptides encoded by these genes can be applied as agrochemical formulations to plants suffering from microbial diseases such as fungal diseases.

16 Claims, 6 Drawing Sheets

Presence in *Brassica rapa*

```
Query= ARACIN2 full length CDS
       (249 nt)
```

>Scaffold000258 2010-07-14
         Length = 46842

Score = 81.3 bits (171), Expect(2) = 4e-17
 Identities = 34/50 (68%), Positives = 37/50 (74%)
 Frame = +1 / +1

Query: 100   MGPAIYTPPSGSCGAPISKYDFQVLAKRPPPCRRPRLENTEDVTHTTRP* 249
             M P I TPPSGSCGA I+K D     R PPCRRPRL+N+EDVTHTT P*
Sbjct: 13072 MVPEISTPPSGSCGAAIAKDDSPQTLARRPPCRRPRLQNSEDVTHTTLP* 13221

>Scaffold000104 2010-07-14
         Length = 773703

Score = 43.2 bits (88), Expect(3) = 1e-09
 Identities = 17/28 (60%), Positives = 21/28 (75%)
 Frame = +1 / -1

Query: 166  QVLAKRPPPCRRPRLENTEDVTHTTRP* 249
            +VLA+R PPCRRPRL+N    +H T P*
Sbjct: 9096 EVLARRSPPCRRPRLQNP*YTSHATVP* 9013

```
Query= ARACIN1 full length CDS
       (231 nt)
```

>Scaffold000258 2010-07-14
         Length = 46842

Score = 57.0 bits (118), Expect(2) = 9e-18
 Identities = 22/23 (95%), Positives = 22/23 (95%)
 Frame = +1 / +1

Query: 163   RAPPCRRPRLQNSEDVTHTTLP* 231
             R PPCRRPRLQNSEDVTHTTLP*
Sbjct: 13153 RRPPCRRPRLQNSEDVTHTTLP* 13221

>Scaffold000104 2010-07-14
         Length = 773703

Score = 82.6 bits (174), Expect(2) = 9e-17
 Identities = 33/54 (61%), Positives = 42/54 (77%)
 Frame = +1 / -1

Query: 70   RSDTGPDISTPPSGSCGASIAEFNSSQILAKRAPPCRRPRLQNSEDVTHTTLP* 231
            R +TGP I TPPSGSC   IA+ +SS++LA+R PPCRRPRLQN    +H T+P*
Sbjct: 9174 RYETGPYIHTPPSGSCRGGIAKQDSSEVLARRSPPCRRPRLQN*YTSHATVP* 9013

SEQUENCE LISTING

<160> NUMBER OF SEQ ID NOS: 65

<210> SEQ ID NO 1
<211> LENGTH: 231
<212> TYPE: DNA
<213> ORGANISM: Arabidopsis thaliana

<400> SEQUENCE: 1

```
atggcgatga agacatcaca tgttcttctg ctttgtttga tgtttgtgat tggttttgta      60
gaagctagaa gatcagatac gggtccggat ataagtactc caccatcagg atcatgtgga     120
gcttcaattg cagaattcaa ttcatcacaa atactagcca agagagcacc accatgtaga     180
cgtcctcgac tccaaaactc agaagatgtg acccacacta cacttccttg a              231
```

<210> SEQ ID NO 2
<211> LENGTH: 40
<212> TYPE: PRT
<213> ORGANISM: Arabidopsis thaliana

<400> SEQUENCE: 2

Gly Ser Cys Gly Ala Ser Ile Ala Glu Phe Asn Ser Ser Gln Ile Leu
1               5                   10                  15

Ala Lys Arg Ala Pro Pro Cys Arg Arg Pro Arg Leu Gln Asn Ser Glu
            20                  25                  30

Asp Val Thr His Thr Thr Leu Pro
        35                  40

<210> SEQ ID NO 3
<211> LENGTH: 249
<212> TYPE: DNA
<213> ORGANISM: Arabidopsis thaliana

<400> SEQUENCE: 3

```
atggcgatga agaatacatc acatgttctt ttgctaagtc ttctgctttg cctgatgttt      60
gtgattggtc ttagaagc tagtatacca gatgacgata tgggtccagc aatatatact      120
ccaccatcag gatcatgtgg agctcctatt tccaaatatg atttccaagt actagccaag     180
agaccaccac catgtagacg tcctcgactc gaaaacacag aagatgtgac ccatactaca     240
cgaccttga                                                              249
```

```
<210> SEQ ID NO 4
<211> LENGTH: 39
<212> TYPE: PRT
<213> ORGANISM: Arabidopsis thaliana

<400> SEQUENCE: 4

Gly Ser Cys Gly Ala Pro Ile Ser Lys Tyr Asp Phe Gln Val Leu Ala
1               5                   10                  15

Lys Arg Pro Pro Pro Cys Arg Arg Pro Arg Leu Glu Asn Thr Glu Asp
            20                  25                  30

Val Thr His Thr Thr Arg Pro
        35

<210> SEQ ID NO 5
<211> LENGTH: 76
<212> TYPE: PRT
<213> ORGANISM: Arabidopsis thaliana

<400> SEQUENCE: 5

Met Ala Met Lys Thr Ser His Val Leu Leu Cys Leu Met Phe Val
1               5                   10                  15

Ile Gly Phe Val Glu Ala Arg Arg Ser Asp Thr Gly Pro Asp Ile Ser
            20                  25                  30

Thr Pro Pro Ser Gly Ser Cys Gly Ala Ser Ile Ala Glu Phe Asn Ser
        35                  40                  45

Ser Gln Ile Leu Ala Lys Arg Ala Pro Pro Cys Arg Arg Pro Arg Leu
    50                  55                  60

Gln Asn Ser Glu Asp Val Thr His Thr Thr Leu Pro
65                  70                  75

<210> SEQ ID NO 6
<211> LENGTH: 54
<212> TYPE: PRT
<213> ORGANISM: Arabidopsis thaliana

<400> SEQUENCE: 6

Arg Arg Ser Asp Thr Gly Pro Asp Ile Ser Thr Pro Pro Ser Gly Ser
1               5                   10                  15

Cys Gly Ala Ser Ile Ala Glu Phe Asn Ser Ser Gln Ile Leu Ala Lys
            20                  25                  30

Arg Ala Pro Pro Cys Arg Arg Pro Arg Leu Gln Asn Ser Glu Asp Val
        35                  40                  45

Thr His Thr Thr Leu Pro
    50

<210> SEQ ID NO 7
<211> LENGTH: 82
<212> TYPE: PRT
<213> ORGANISM: Arabidopsis thaliana

<400> SEQUENCE: 7

Met Ala Met Lys Asn Thr Ser His Val Leu Leu Leu Ser Leu Leu Leu
1               5                   10                  15

Cys Leu Met Phe Val Ile Gly Leu Val Glu Ala Ser Ile Pro Asp Asp
            20                  25                  30

Asp Met Gly Pro Ala Ile Tyr Thr Pro Pro Ser Gly Ser Cys Gly Ala
        35                  40                  45

Pro Ile Ser Lys Tyr Asp Phe Gln Val Leu Ala Lys Arg Pro Pro Pro
```

```
              50                  55                  60
Cys Arg Arg Pro Arg Leu Glu Asn Thr Glu Asp Val Thr His Thr Thr
 65                  70                  75                  80

Arg Pro

<210> SEQ ID NO 8
<211> LENGTH: 55
<212> TYPE: PRT
<213> ORGANISM: Arabidopsis thaliana

<400> SEQUENCE: 8

Ser Ile Pro Asp Asp Met Gly Pro Ala Ile Tyr Thr Pro Pro Ser
  1               5                  10                  15

Gly Ser Cys Gly Ala Pro Ile Ser Lys Tyr Asp Phe Gln Val Leu Ala
                 20                  25                  30

Lys Arg Pro Pro Pro Cys Arg Arg Pro Arg Leu Glu Asn Thr Glu Asp
             35                  40                  45

Val Thr His Thr Thr Arg Pro
             50                  55

<210> SEQ ID NO 9
<211> LENGTH: 50
<212> TYPE: DNA
<213> ORGANISM: Artificial Sequence
<220> FEATURE:
<223> OTHER INFORMATION: Primer

<400> SEQUENCE: 9
ggggacaagt ttgtacaaaa aagcaggctt ctaacttatt tgcagggaac           50

<210> SEQ ID NO 10
<211> LENGTH: 48
<212> TYPE: DNA
<213> ORGANISM: Artificial Sequence
<220> FEATURE:
<223> OTHER INFORMATION: Primer

<400> SEQUENCE: 10
ggggaccact ttgtacaaga aagctgggtc caaacaaagc agaagaac              48

<210> SEQ ID NO 11
<211> LENGTH: 49
<212> TYPE: DNA
<213> ORGANISM: Artificial Sequence
<220> FEATURE:
<223> OTHER INFORMATION: Primer

<400> SEQUENCE: 11
ggggaccact ttgtacaaga aagctgggtc tggctcttct tatctcaag            49

<210> SEQ ID NO 12
<211> LENGTH: 53
<212> TYPE: DNA
<213> ORGANISM: Artificial Sequence
<220> FEATURE:
<223> OTHER INFORMATION: Primer

<400> SEQUENCE: 12
ggggacaagt ttgtacaaaa aagcaggctt caaactagaa atgtttcaag aag       53

<210> SEQ ID NO 13
<211> LENGTH: 52
<212> TYPE: DNA
```

```
<213> ORGANISM: Artificial Sequence
<220> FEATURE:
<223> OTHER INFORMATION: Primer

<400> SEQUENCE: 13
ggggaccact ttgtacaaga aagctgggtc tggctcttct atcttaaata ac          52

<210> SEQ ID NO 14
<211> LENGTH: 50
<212> TYPE: DNA
<213> ORGANISM: Artificial Sequence
<220> FEATURE:
<223> OTHER INFORMATION: Primer

<400> SEQUENCE: 14
ggggacaagt ttgtacaaaa aagcaggctt catggcgatg aagacatcac             50

<210> SEQ ID NO 15
<211> LENGTH: 60
<212> TYPE: DNA
<213> ORGANISM: Artificial Sequence
<220> FEATURE:
<223> OTHER INFORMATION: Primer

<400> SEQUENCE: 15
ggggacaagt ttgtacaaaa aagcaggctc catgtttgtg attggttttg tagaagctag  60

<210> SEQ ID NO 16
<211> LENGTH: 54
<212> TYPE: DNA
<213> ORGANISM: Artificial Sequence
<220> FEATURE:
<223> OTHER INFORMATION: Primer

<400> SEQUENCE: 16
ggggaccact ttgtacaaga aagctgggtc tcaaggaagt gtagtgtggg tcac        54

<210> SEQ ID NO 17
<211> LENGTH: 57
<212> TYPE: DNA
<213> ORGANISM: Artificial Sequence
<220> FEATURE:
<223> OTHER INFORMATION: Primer

<400> SEQUENCE: 17
ggggaccact ttgtacaaga aagctgggtc aggaagtgta gtgtgggtca catcttc     57

<210> SEQ ID NO 18
<211> LENGTH: 53
<212> TYPE: DNA
<213> ORGANISM: Artificial Sequence
<220> FEATURE:
<223> OTHER INFORMATION: Primer

<400> SEQUENCE: 18
ggggacaagt ttgtacaaaa aagcaggctt catggcgatg aagaatacat cac         53

<210> SEQ ID NO 19
<211> LENGTH: 52
<212> TYPE: DNA
<213> ORGANISM: Artificial Sequence
<220> FEATURE:
<223> OTHER INFORMATION: Primer

<400> SEQUENCE: 19
ggggaccact ttgtacaaga aagctgggtc tcaaggtcgt gtagtatggg tc          52
```

<210> SEQ ID NO 20
<211> LENGTH: 51
<212> TYPE: DNA
<213> ORGANISM: Artificial Sequence
<220> FEATURE:
<223> OTHER INFORMATION: Primer

<400> SEQUENCE: 20
ggggaccact tgtacaaga aagctgggtc aggtcgtgta gtatgggtca c        51

<210> SEQ ID NO 21
<211> LENGTH: 40
<212> TYPE: DNA
<213> ORGANISM: Artificial Sequence
<220> FEATURE:
<223> OTHER INFORMATION: Primer

<400> SEQUENCE: 21
gataggacgt ctacatggtg gtctctctct tttgtattcc                    40

<210> SEQ ID NO 22
<211> LENGTH: 40
<212> TYPE: DNA
<213> ORGANISM: Artificial Sequence
<220> FEATURE:
<223> OTHER INFORMATION: Primer

<400> SEQUENCE: 22
gagaccacca tgtagacgtc ctatcaaaga gaatcaatga                    40

<210> SEQ ID NO 23
<211> LENGTH: 40
<212> TYPE: DNA
<213> ORGANISM: Artificial Sequence
<220> FEATURE:
<223> OTHER INFORMATION: Primer

<400> SEQUENCE: 23
gagaacacca tgtagtcgtc ctttcacagg tcgtgatatg                    40

<210> SEQ ID NO 24
<211> LENGTH: 40
<212> TYPE: DNA
<213> ORGANISM: Artificial Sequence
<220> FEATURE:
<223> OTHER INFORMATION: Primer

<400> SEQUENCE: 24
gaaaggacga ctacatggtg ttctctacat atatattcct                    40

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
gtagaagcta gaagatcaga tac                                      23

<210> SEQ ID NO 26
<211> LENGTH: 19
<212> TYPE: DNA
<213> ORGANISM: Artificial Sequence
<220> FEATURE:

<223> OTHER INFORMATION: Primer

<400> SEQUENCE: 26
tcaaggaagt gtagtgtgg                                                        19

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
ctaagtcttc tgctttgcct gatg                                                  24

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28
cgtctacatg gtggtggtct c                                                     21

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
attttgccga tttcggaac                                                        19

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
tggttcacgt agtgggccat cg                                                    22

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
tccacatgtc atcaccttct c                                                     21

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
gagtcgagga cgtctacatg g                                                     21

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
agacgatttc acattgccat c                                    21

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
agataagaag agccaatggc g                                    21

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
tgatcctcgt gggaattatg t                                    21

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
tgcatgatca catcattact tcat                                 24

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
gactgtggcg gtctaagatg t                                    21

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tgaattcagc cagagtgacg                                      20

<210> SEQ ID NO 39
<211> LENGTH: 20
<212> TYPE: DNA
<213> ORGANISM: Artificial Sequence
<220> FEATURE:
<223> OTHER INFORMATION: Primer

```
<400> SEQUENCE: 39
ctggtcatgg cacaagttca                                          20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
gccatttcta gcttggttgg                                          20

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
tgaccactct ccaaaacttt gac                                      23

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
cttttaactg cggcggtaga                                          20

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
gttctctttg ctgctttcga c                                        21

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
gcaaacccct gaccatgt                                            18

<210> SEQ ID NO 45
<211> LENGTH: 28
<212> TYPE: DNA
<213> ORGANISM: Artificial Sequence
<220> FEATURE:
<223> OTHER INFORMATION: Primer

<400> SEQUENCE: 45
tcaaggaagt gtagtgtggg tcacatct                                 28

<210> SEQ ID NO 46
<211> LENGTH: 25
```

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
tctgagtttt ggagtcgagg acgtc        25

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
caggatcatg tggagcttca attgc        25

<210> SEQ ID NO 48
<211> LENGTH: 30
<212> TYPE: DNA
<213> ORGANISM: Artificial Sequence
<220> FEATURE:
<223> OTHER INFORMATION: Primer

<400> SEQUENCE: 48
caattcatca caaatactag ccaagagagc        30

<210> SEQ ID NO 49
<211> LENGTH: 27
<212> TYPE: DNA
<213> ORGANISM: Artificial Sequence
<220> FEATURE:
<223> OTHER INFORMATION: Primer

<400> SEQUENCE: 49
caccaagcag tggtatcaac gcagagt        27

<210> SEQ ID NO 50
<211> LENGTH: 83
<212> TYPE: PRT
<213> ORGANISM: Arabidopsis lyrata

<400> SEQUENCE: 50

Met Ala Met Lys Lys Thr Ser His Val Leu Leu Ser Leu Leu
1               5                   10                  15

Cys Leu Met Phe Val Ile Gly Leu Val Glu Ala Ser Ile Pro Gly Gly
            20                  25                  30

Asp Met Gly Pro Glu Ile Tyr Thr Pro Pro Ser Gly Ser Cys Gly Ala
        35                  40                  45

Pro Ile Ala Lys Tyr Asp Ser Gln Val Leu Leu Thr Lys Arg Pro Pro
    50                  55                  60

Pro Cys Arg Arg Pro Arg Leu Glu Asn Thr Glu Asp Val Thr Tyr Thr
65                  70                  75                  80

Thr Arg Pro

<210> SEQ ID NO 51
<211> LENGTH: 78
<212> TYPE: PRT
<213> ORGANISM: Arabidopsis lyrata

<400> SEQUENCE: 51

Met Ala Met Lys Thr Ser His Val Leu Leu Leu Cys Leu Val Phe Val

```
            1               5                  10                  15
Ile Gly Leu Val Glu Ala Arg Ile Ser Gly Gly Asp Met Gly Pro Glu
                20                  25                  30

Ile Arg Thr Pro Pro Ser Gly Ser Cys Gly Ala Ser Ile Ala Glu Tyr
                35                  40                  45

Asp Ser Ser Arg Val Leu Ala Lys Arg Pro Pro Cys Arg Arg Pro
 50                  55                  60

Arg Pro Gln Asn Gln Glu Asp Val Thr His Thr Leu Pro
 65                  70                  75
```

<210> SEQ ID NO 52
<211> LENGTH: 78
<212> TYPE: PRT
<213> ORGANISM: Artificial
<220> FEATURE:
<223> OTHER INFORMATION: Polypeptide consensus sequence

<400> SEQUENCE: 52

```
Thr Ser His Val Leu Leu Leu Ser Leu Leu Cys Leu Met Phe Val
 1               5                  10                  15

Ile Gly Leu Val Glu Ala Ser Ile Ser Gly Gly Asp Met Gly Pro Glu
                20                  25                  30

Ile Tyr Thr Pro Pro Ser Gly Ser Cys Gly Ala Ser Ile Ala Lys Tyr
                35                  40                  45

Asp Ser Ser Gln Val Leu Ala Lys Arg Pro Pro Cys Arg Arg Pro
 50                  55                  60

Arg Leu Gln Asn Thr Glu Asp Val Thr His Thr Arg Pro
 65                  70                  75
```

<210> SEQ ID NO 53
<211> LENGTH: 49
<212> TYPE: PRT
<213> ORGANISM: Arabidopsis thaliana

<400> SEQUENCE: 53

```
Met Gly Pro Ala Ile Tyr Thr Pro Pro Ser Gly Ser Cys Gly Ala Pro
 1               5                  10                  15

Ile Ser Lys Tyr Asp Phe Gln Val Leu Ala Lys Arg Pro Pro Cys
                20                  25                  30

Arg Arg Pro Arg Leu Glu Asn Thr Glu Asp Val Thr His Thr Arg
                35                  40                  45

Pro
```

<210> SEQ ID NO 54
<211> LENGTH: 49
<212> TYPE: PRT
<213> ORGANISM: Brassica rapa

<400> SEQUENCE: 54

```
Met Val Pro Glu Ile Ser Thr Pro Pro Ser Gly Ser Cys Gly Ala Ala
 1               5                  10                  15

Ile Ala Lys Asp Asp Ser Pro Gln Thr Leu Ala Arg Arg Pro Pro Cys
                20                  25                  30

Arg Arg Pro Arg Leu Gln Asn Ser Glu Asp Val Thr His Thr Thr Leu
                35                  40                  45

Pro
```

<210> SEQ ID NO 55

```
<211> LENGTH: 27
<212> TYPE: PRT
<213> ORGANISM: Arabidopsis thaliana

<400> SEQUENCE: 55

Gln Val Leu Ala Lys Arg Pro Pro Cys Arg Arg Pro Arg Leu Glu
1               5                   10                  15

Asn Thr Glu Asp Val Thr His Thr Thr Arg Pro
            20                  25

<210> SEQ ID NO 56
<211> LENGTH: 26
<212> TYPE: PRT
<213> ORGANISM: Brassica rapa

<400> SEQUENCE: 56

Glu Val Leu Ala Arg Arg Ser Pro Pro Cys Arg Arg Pro Arg Leu Gln
1               5                   10                  15

Asn Pro Tyr Thr Ser His Ala Thr Val Pro
            20                  25

<210> SEQ ID NO 57
<211> LENGTH: 22
<212> TYPE: PRT
<213> ORGANISM: Arabidopsis thaliana

<400> SEQUENCE: 57

Arg Ala Pro Pro Cys Arg Arg Pro Arg Leu Gln Asn Ser Glu Asp Val
1               5                   10                  15

Thr His Thr Thr Leu Pro
            20

<210> SEQ ID NO 58
<211> LENGTH: 22
<212> TYPE: PRT
<213> ORGANISM: Brassica rapa

<400> SEQUENCE: 58

Arg Arg Pro Pro Cys Arg Arg Pro Arg Leu Gln Asn Ser Glu Asp Val
1               5                   10                  15

Thr His Thr Thr Leu Pro
            20

<210> SEQ ID NO 59
<211> LENGTH: 53
<212> TYPE: PRT
<213> ORGANISM: Arabidopsis thaliana

<400> SEQUENCE: 59

Arg Ser Asp Thr Gly Pro Asp Ile Ser Thr Pro Pro Ser Gly Ser Cys
1               5                   10                  15

Gly Ala Ser Ile Ala Glu Phe Asn Ser Ser Gln Ile Leu Ala Lys Arg
            20                  25                  30

Ala Pro Pro Cys Arg Arg Pro Arg Leu Gln Asn Ser Glu Asp Val Thr
        35                  40                  45

His Thr Thr Leu Pro
    50

<210> SEQ ID NO 60
<211> LENGTH: 52
<212> TYPE: PRT
<213> ORGANISM: Brassica rapa
```

-continued

<400> SEQUENCE: 60

Arg Tyr Glu Thr Gly Pro Tyr Ile His Thr Pro Pro Ser Gly Ser Cys
1               5                   10                  15

Arg Gly Gly Ile Ala Lys Gln Asp Ser Ser Glu Val Leu Ala Arg Arg
            20                  25                  30

Ser Pro Pro Cys Arg Arg Pro Arg Leu Gln Asn Pro Tyr Thr Ser His
        35                  40                  45

Ala Thr Val Pro
    50

<210> SEQ ID NO 61
<211> LENGTH: 49
<212> TYPE: PRT
<213> ORGANISM: Artificial
<220> FEATURE:
<223> OTHER INFORMATION: ARACIN2 sequence alignment with Brassica rapa
      ortholog
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (16)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = any amino acid
<220> FEATURE:
<221> NAME/KEY: MISC_FEATURE
<222> LOCATION: (24)..(24)
<223> OTHER INFORMATION: Xaa = any amino acid
<220> FEATURE:
<221> NAME/KEY: MISC_FEATURE
<222> LOCATION: (25)..(25)
<223> OTHER INFORMATION: Xaa = any amino acid
<220> FEATURE:
<221> NAME/KEY: MISC_FEATURE
<222> LOCATION: (26)..(26)
<223> OTHER INFORMATION: Xaa = any amino acid
<220> FEATURE:
<221> NAME/KEY: MISC_FEATURE
<222> LOCATION: (27)..(27)
<223> OTHER INFORMATION: Xaa = any amino acid
<220> FEATURE:
<221> NAME/KEY: MISC_FEATURE
<222> LOCATION: (29)..(29)
<223> OTHER INFORMATION: Xaa = any amino acid
<220> FEATURE:
<221> NAME/KEY: MISC_FEATURE
<222> LOCATION: (38)..(38)
<223> OTHER INFORMATION: Xaa = any amino acid

```
<220> FEATURE:
<221> NAME/KEY: MISC_FEATURE
<222> LOCATION: (40)..(40)
<223> OTHER INFORMATION: Xaa = any amino acid
<220> FEATURE:
<221> NAME/KEY: MISC_FEATURE
<222> LOCATION: (48)..(48)
<223> OTHER INFORMATION: Xaa = any amino acid

<400> SEQUENCE: 61

Met Xaa Pro Xaa Ile Xaa Thr Pro Pro Ser Gly Ser Cys Gly Ala Xaa
1               5                   10                  15

Ile Xaa Lys Xaa Asp Xaa Xaa Xaa Xaa Xaa Xaa Arg Xaa Pro Pro Cys
            20                  25                  30

Arg Arg Pro Arg Leu Xaa Asn Xaa Glu Asp Val Thr His Thr Thr Xaa
        35                  40                  45

Pro

<210> SEQ ID NO 62
<211> LENGTH: 26
<212> TYPE: PRT
<213> ORGANISM: Artificial
<220> FEATURE:
<223> OTHER INFORMATION: ARACIN2 sequence alignment with Brassica rapa
      ortholog
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = any amino acid
<220> FEATURE:
<221> NAME/KEY: MISC_FEATURE
<222> LOCATION: (25)..(25)
<223> OTHER INFORMATION: Xaa = any amino acid

<400> SEQUENCE: 62

Val Leu Ala Xaa Arg Xaa Pro Pro Cys Arg Arg Pro Arg Leu Xaa Asn
1               5                   10                  15

Xaa Xaa Xaa Xaa Xaa His Xaa Thr Xaa Pro
            20                  25
```

```
<210> SEQ ID NO 63
<211> LENGTH: 22
<212> TYPE: PRT
<213> ORGANISM: Artificial
<220> FEATURE:
<223> OTHER INFORMATION: ARACIN1 sequence alignment with Brassica rapa
      ortholog
<220> FEATURE:
<221> NAME/KEY: MISC_FEATURE
<222> LOCATION: (2)..(2)
<223> OTHER INFORMATION: Xaa = any amino acid

<400> SEQUENCE: 63

Arg Xaa Pro Pro Cys Arg Arg Pro Arg Leu Gln Asn Ser Glu Asp Val
1               5                   10                  15

Thr His Thr Thr Leu Pro
            20

<210> SEQ ID NO 64
<211> LENGTH: 53
<212> TYPE: PRT
<213> ORGANISM: Artificial
<220> FEATURE:
<223> OTHER INFORMATION: ARACIN1 sequence alignment with Brassica rapa
      ortholog
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = any amino acid
<220> FEATURE:
<221> NAME/KEY: MISC_FEATURE
<222> LOCATION: (24)..(24)
<223> OTHER INFORMATION: Xaa = any amino acid
<220> FEATURE:
<221> NAME/KEY: MISC_FEATURE
<222> LOCATION: (27)..(27)
<223> OTHER INFORMATION: Xaa = any amino acid
<220> FEATURE:
<221> NAME/KEY: MISC_FEATURE
<222> LOCATION: (28)..(28)
<223> OTHER INFORMATION: Xaa = any amino acid
<220> FEATURE:
<221> NAME/KEY: MISC_FEATURE
```

```
<222> LOCATION: (31)..(31)
<223> OTHER INFORMATION: Xaa = any amino acid
<220> FEATURE:
<221> NAME/KEY: MISC_FEATURE
<222> LOCATION: (33)..(33)
<223> OTHER INFORMATION: Xaa = any amino acid
<220> FEATURE:
<221> NAME/KEY: MISC_FEATURE
<222> LOCATION: (44)..(44)
<223> OTHER INFORMATION: Xaa = any amino acid
<220> FEATURE:
<221> NAME/KEY: MISC_FEATURE
<222> LOCATION: (45)..(45)
<223> OTHER INFORMATION: Xaa = any amino acid
<220> FEATURE:
<221> NAME/KEY: MISC_FEATURE
<222> LOCATION: (46)..(46)
<223> OTHER INFORMATION: Xaa = any amino acid
<220> FEATURE:
<221> NAME/KEY: MISC_FEATURE
<222> LOCATION: (47)..(47)
<223> OTHER INFORMATION: Xaa = any amino acid
<220> FEATURE:
<221> NAME/KEY: MISC_FEATURE
<222> LOCATION: (48)..(48)
<223> OTHER INFORMATION: Xaa = any amino acid
<220> FEATURE:
<221> NAME/KEY: MISC_FEATURE
<222> LOCATION: (50)..(50)
<223> OTHER INFORMATION: Xaa = any amino acid
<220> FEATURE:
<221> NAME/KEY: MISC_FEATURE
<222> LOCATION: (52)..(52)
<223> OTHER INFORMATION: Xaa = any amino acid

<400> SEQUENCE: 64

Arg Xaa Xaa Thr Gly Pro Xaa Ile Xaa Thr Pro Pro Ser Gly Ser Cys
 1               5                  10                  15

Xaa Xaa Xaa Ile Ala Xaa Xaa Xaa Ser Ser Xaa Xaa Leu Ala Xaa Arg
            20                  25                  30

Xaa Pro Pro Cys Arg Arg Pro Arg Leu Gln Asn Xaa Xaa Xaa Xaa Xaa
        35                  40                  45

His Xaa Thr Xaa Pro
    50

<210> SEQ ID NO 65
<211> LENGTH: 40
<212> TYPE: PRT
<213> ORGANISM: Artificial
<220> FEATURE:
<223> OTHER INFORMATION: At25 to At20 consensus sequence
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = any amino acid
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (12)..(12)
```

```
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (29)..(29)
<223> OTHER INFORMATION: Xaa = any amino acid
<220> FEATURE:
<221> NAME/KEY: MISC_FEATURE
<222> LOCATION: (31)..(31)
<223> OTHER INFORMATION: Xaa = any amino acid
<220> FEATURE:
<221> NAME/KEY: MISC_FEATURE
<222> LOCATION: (38)..(38)
<223> OTHER INFORMATION: Xaa = any amino acid
<220> FEATURE:
<221> NAME/KEY: misc_feature
<222> LOCATION: (39)..(39)
<223> OTHER INFORMATION: Xaa can be any naturally occurring amino acid

<400> SEQUENCE: 65

Gly Ser Cys Gly Ala Xaa Ile Xaa Xaa Xaa Xaa Xaa Xaa Gln Xaa Leu
1               5                   10                  15

Ala Lys Arg Xaa Pro Pro Cys Arg Arg Pro Arg Leu Xaa Asn Xaa Glu
            20                  25                  30

Asp Val Thr His Thr Thr Xaa Pro
            35                  40
```

METHODS AND MEANS FOR GENERATING MICROBIAL DISEASE RESISTANT PLANTS

CROSS-REFERENCE TO RELATED APPLICATIONS

This application is a national phase entry under 35 U.S.C. §371 of International Patent Application PCT/EP2013/058513, filed May 9, 2013, designating the United States of America and published in English as International Patent Publication WO2012/152816 A1 on Nov. 15, 2012, which claims the benefit under Article 8 of the Patent Cooperation Treaty and under 35 U.S.C. §119(e) to U.S. Provisional Patent Application Ser. No. 61/518,832, filed May 11, 2011.

TECHNICAL FIELD

The disclosure relates to the field of plant molecular biology, more particularly to the field of agriculture, and more specifically to the field of microbial disease resistance in plants, in particular fungal disease resistance. Provided are genes and chimeric genes encoding antimicrobial peptides. These genes can be used to generate transgenic plants with an improved resistance to, for example, plant pathogenic fungi. Alternatively, the peptides encoded by these genes can be applied as agrochemical formulations to plants suffering from microbial diseases such as fungal diseases.

BACKGROUND

Pests, weeds and diseases cause a yearly loss of around 30% of the world's agricultural production. Fungal diseases have been one of the principal causes of crop losses ever since humans started to cultivate plants. To date, the epidemic spread of fungal diseases is controlled by i) various crop husbandry techniques, such as crop rotation and avoiding the spread of infested soil and pathogen-carrying plant materials, ii) breeding of fungus-resistant cultivars of crops, and iii) the application of agrochemicals. Although breeders have succeeded in producing cultivars resistant to fungal diseases, the time-consuming processes of making crosses and backcrosses and the selection of progenies for the presence of resistance traits make it difficult to react adequately to the evolution of new virulent fungal races. Therefore, farmers often have to use chemicals. Agrochemicals are costly, and eventually they become less efficient due to the evolution of the pathogen. In addition, both their production and their persistence in the soil after use are potentially harmful to the environment. The growing concern about the environment, together with a strong motivation to lower production costs, encourages the development of crops that require fewer chemicals. To protect themselves against pathogens, plants produce various antimicrobial compounds, either secondary metabolites or proteins, whose production can be either constitutive or inducible upon pathogen perception. Successful pathogens have found effective ways to avoid or resist contact with these antimicrobial compounds. Taking into consideration that these compounds and the ways they are produced strongly differ from plant to plant, it is not surprising that most pathogens are highly specialized and have a very narrow host range, often limited to one species or even to certain genotypes within that species. During the last decade, several research groups have discovered plant genes (antifungal genes), which directly or indirectly limit the growth of fungal pathogens. In several documented cases, it is found that overexpression of such antifungal genes in plants confers resistance to one or more fungal pathogens. There is, however, a need for the identification of novel antifungal peptides, which can be used to combat fungi by generating either transgenic plants or applying these antifungal peptides directly to plants.

SUMMARY OF THE DISCLOSURE

This disclosure satisfies those needs and provides antifungal peptides that have been isolated from *Arabidopsis thaliana*.

BRIEF DESCRIPTION OF THE DRAWINGS

FIG. 3: Sequence alignment of At5g36925+5' (SEQ ID NO: 1) similar region and At5g36920 (SEQ ID NO: 3). Sequence analysis showed that At5g36925 has a sequence of 54 nucleotides upstream of the annotated start codon which displays high similarity with the 5' CDS of At5g36920. Gaps are always in nucleotide triplets supporting our findings that this sequence can be translated.

FIG. 4: Protein sequence alignment of At5g36925+5' (SEQ ID NO: 5) similar region and At5g36920 (SEQ ID NO: 7). Sequence alignment of the translated At5g36925+5' (SEQ ID NO: 5) similar region with the protein sequence of At5g36920 (SEQ ID NO: 7) shows a high degree of similarity.

FIG. 5: Multiple protein sequence alignment. Comparative analysis using PLAZA (Proost S. et al. (2010) The Plant Cell Online 21, 3718-3731) indicates two paralogs of At5g36925 (SEQ ID NO: 5) and At5g36920 (SEQ ID NO: 7) are present in *Arabidopsis lyrata* (SEQ ID NOS: 51 and 50, respectively).

The consensus sequence (SEQ ID NO: 52) is also shown.

Figure 6:
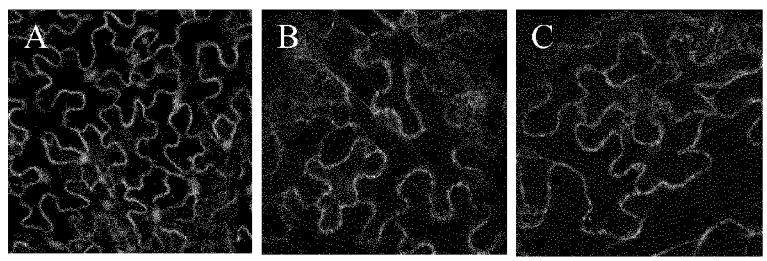

FIG. 6: The subcellular localization of At5g36925 and At5g36920. (A) Transient expression of the C-terminal GFP-fusion of At5g36925 in the epidermis of *N. benthamiana* reveals a nucleocytoplasmic localization. (B) Addition of the 5' similar region drastically affects the localization of At5g36925. As expected, this 5' similar region contains a signal peptide which targets the peptide to the secretory pathway. (C) The C-terminal GFP-fusion of At5g36920 is targeted to the secretory pathway.

Figure 7:

FIG. 7: Synteny plot of At5g36925 and At5g36920. The synteny plot displays the spatial organization in the genome of homologous genes. Since At5g36925 and At5g36920 are the result of a recent tandem duplication, they are highly similar paralogs. Both genes are flanked by defense-related genes: a TIR-NBS class protein (At5g36930) and a thionin (At5g36910, Thi2.2). It is well known that many defense-related genes are positioned in clusters to ensure synchronous expression during pathogen infection. Therefore, a defense role of At5g36925 and At5g36920 could be implied.

Figure 8:
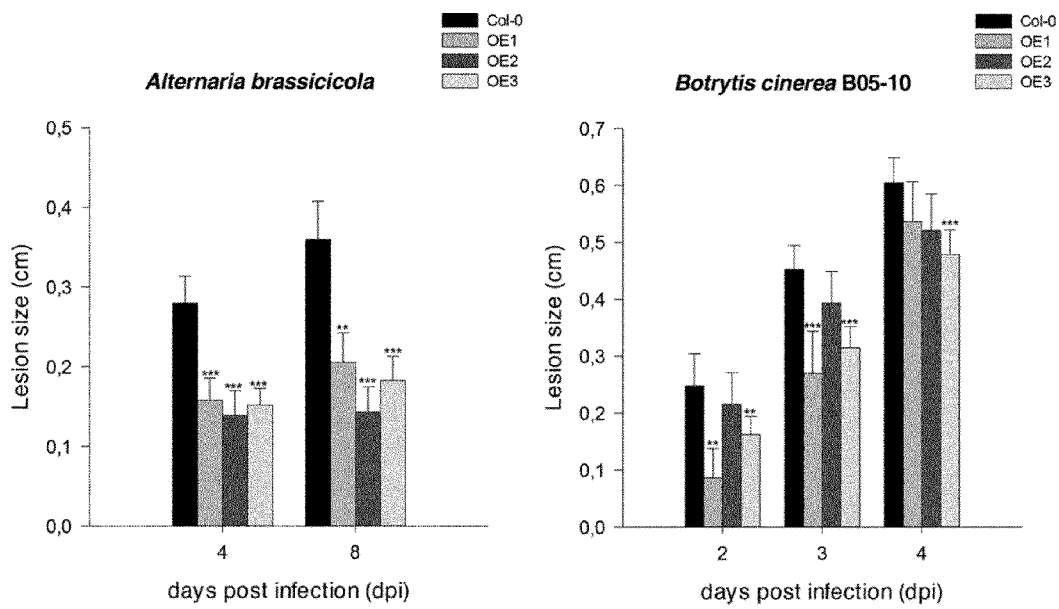

FIG. 8: Decreased sensitivity upon *A. brassicicola* and *B. cinerea* infection by overexpression of At25. Lesion sizes on leaves of wild-type plants and three independent At25OE lines measured several days after inoculation with *A. brassicicola* and *B. cinerea* B05-10. Data presented are the means of at least 50 lesions. Error bars represent 95% confidence intervals (n=~50). For each assay, the average lesion diameter of wild-type and mutant plants were compared with a Student's t-test (*, $p<0.05$; , $p<0.01$; *, $p<0.001$). The disease assays were done in duplicate, with similar results.

Figure 9:
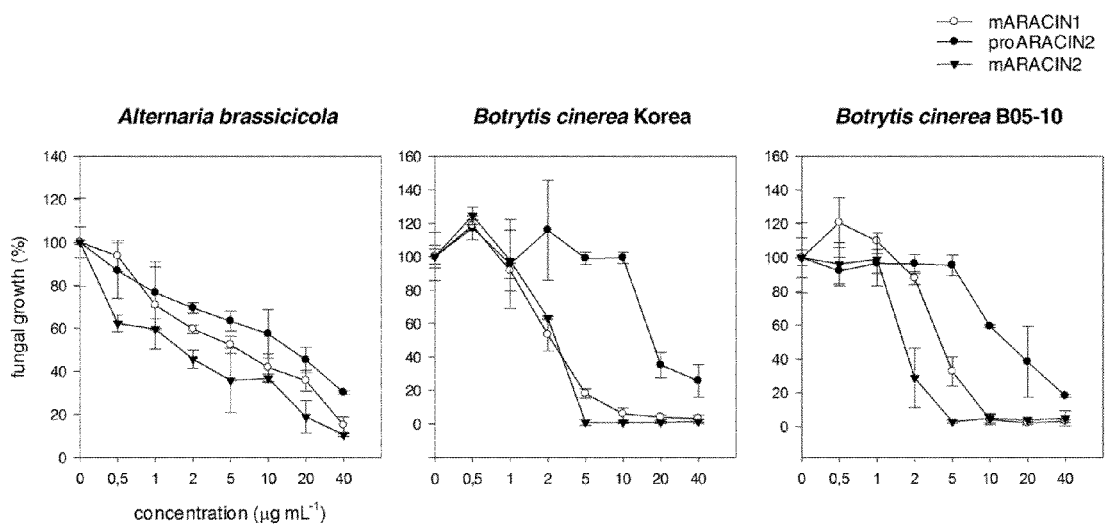

FIG. 9: Inhibitory effects of mature peptide At25 (SEQ ID NO: 2, also depicted in the figure as mARACIN1), propeptide of At20 (SEQ ID NO: 8, also depicted in the figure as proARACIN2) and mature At20 peptide (SEQ ID NO: 4, also depicted in the figure as mARACIN2) on the growth of *A. brassicicola*, *B. cinerea* Korea and *B. cinerea* B05-10. The data is represented as a mean±SE (n=2). The antifungal assays were done in duplicate, with similar results.

FIG. 10: Multiple protein sequence alignments of At20 (also depicted as ARACIN2 in the figure) (SEQ ID NOS: 53 and 55) and AT25 (also depicted as ARICIN1 in the figure) (SEQ ID NOS: 57 and 59) with the *Brassica rapa* orthologs identified using the *Brassica* Database (BRAD; on the World Wide Web at brassicadb.org/brad/index.php/) (SEQ ID NOS: 54, 56, 58 and 60, respectively, in the figure). The consensus sequence is shown between each sequence alignment (SEQ ID NOS: 61, 62, 63 and 64, respectively, in the figure).

DETAILED DESCRIPTION

Plants have developed a variety of mechanisms to cope with abiotic and biotic stresses in which the production and sensing of reactive oxygen species (ROS) have been shown to play a key role. In a localisome study of hydrogen peroxide-induced proteins we identified two novel secreted peptides which expression is highly regulated by both environmental cues as well as pathogen infection. Both peptides are encoded by two paralogous *Arabidopsis*-specific genes with distinct expression patterns. The encoding genes are positioned in a cluster of defense-related genes and share many features with antimicrobial peptides but lack the characteristic 6-8 cysteine residues. When expressed in transgenic *Arabidopsis* plants, the peptides significantly enhanced resistance against the necrotrophic fungal pathogens *Botrytis cinerea* and *Alternaria brassicicola*.

Accordingly, provided is an isolated polypeptide comprising the amino acid as depicted in SEQ ID NO: 2, or a homologue having at least 60% identity with SEQ ID NO: 2.

In yet another embodiment, provided is an isolated polypeptide comprising the amino acid as depicted in SEQ ID NO: 2, or a homologue having at least 65%, at least 70%, at least 75%, at least 80%, at least 85%, at least 90%, at least 95% identity with SEQ ID NO: 2.

The amino acid sequence of SEQ ID NO: 2 is depicted in the following sequence: NH2-GSCGASIAEFNSSQILAKRAPPCRRPRLQNSEDVTHTTLP-COOH (see, e.g., SEQ ID NO: 2).

SEQ ID NO: 2 is in the Examples section hereof designated as the mature At25 peptide. SEQ ID NO: 2 is the mature peptide derived after processing of a 76 amino acid pre-pro-peptide (SEQ ID NO: 5).

The amino acid sequence of SEQ ID NO: 5 is depicted in the following sequence: NH2-MAMKTSHVLLLCLM-FVIGFVEARRSDTGPDISTPPSGSCGASIAEFNS SQILAKRAPPCRRPRLQNSEDVTHTTLP-COOH (see, e.g., SEQ ID NO: 5).

It is believed that the pre-pro-peptide is processed into a pro-peptide before the pro-peptide is processed into the mature peptide. The amino acid sequence of SEQ ID NO: 6 depicts the pro-peptide in the following sequence: NH2-RRSDTGPDISTPPSGSCGASIAE FNSSQILAKRAPPCRRPRLQNSEDVTHTTLP-COOH (see, e.g., SEQ ID NO: 6).

In yet another embodiment the invention provides for an isolated polypeptide, which is depicted in SEQ ID NO: 4.

The amino acid sequence of SEQ ID NO: 4 is depicted in the following sequence: NH2-GSCGAPISKYDFQV-LAKRPPPCRRPRLENTEDVTHTTRP-COOH (see, e.g., SEQ ID NO: 4).

SEQ ID NO: 4 is in the examples section designated as the mature At20 peptide. SEQ ID NO: 4 is the mature peptide derived after processing of an 82 amino acid pre-pro-peptide (SEQ ID NO: 7).

The amino acid sequence of the SEQ ID NO: 7 is depicted in the following sequence: NH2-MAMKNTSHV-LLLSLLLCLMFVIGLVEASIPDDDMG-PAIYTPPSGSCGA PISKYDFQVLAKRPPPCR-RPRLENTEDVTHTTRP-COOH (see, e.g., SEQ ID NO: 7).

It is believed that the pre-pro-peptide is processed into a pro-peptide before the pro-peptide is processed into the mature peptide. The amino acid sequence of SEQ ID NO: 8 depicts the pro-peptide in the following sequence: NH2-SIP-DDDMGPAIYTPPSGSCGA PISKYDFQVLAKRPPPCR-RPRLENTEDVTHTTRP-COOH (see, e.g., SEQ ID NO: 8).

The protein sequence similarity between mature peptide At25 (SEQ ID NO: 2) and mature peptide At20 (SEQ ID NO: 4) is calculated as 70% (i.e., 28 identical amino acid residues in a range of 40 amino acid):

```
NW Score = 150
Identities = 28/40 (70%), Positives = 35/40 (88%),
Gaps = 1/40 (3%)

Query 1  GSCGASIAEFNSSQILAKRAPPCRRPRLQNSEDVTHTTLP 40 (SEQ ID NO: 2)
```

```
        GSCGA I++++  Q+LAKR PPCRRPRL+N+EDVTHTT P     (SEQ ID NO: 65)

Sbjct 1 GSCGAPISKYDF-QVLAKRPPPCRRPRLENTEDVTHTTRP 39 (SEQ ID NO: 4)
```

In yet another embodiment, provided is a nucleotide sequence capable of encoding a polypeptide depicted in SEQ ID NO: 2 or a nucleotide sequence encoding a homologue having at least 70% identity with SEQ ID NO: 2. Strictly spoken SEQ ID NO: 1 encodes a pre-pro-sequence as depicted in SEQ ID NO: 5, the pre-pro sequence is further matured in the plant cell to a pro-sequence (SEQ ID NO: 6) which then finally matures in the plant cell into SEQ ID NO: 2.

In yet another embodiment, provided is an isolated DNA molecule depicted in SEQ ID NO: 1 or a homologue of SEQ ID NO: 1 with at least 80% identity.

In yet another embodiment, provided is an isolated DNA molecule depicted in SEQ ID NO: 1 or a homologue of SEQ ID NO: 1 with at least 85% identity.

In yet another embodiment, provided is an isolated DNA molecule depicted in SEQ ID NO: 1 or a homologue of SEQ ID NO: 1 with at least 90%, at least 95% identity.

The nucleotide sequence (coding sequence) of SEQ ID NO: 1 is depicted in the following sequence: 5'-atggcgatgaagacatcacatgttcttctgctttgtttgATGTTTGTGATTGGTTTTGT AGAAGCTAGAAGATCAGATACGGGTCCGGATATAAGTACTCCACCATCAGGATCAT GTGGAGCTTCAATTGCAGAATTCAATTCATCACAAATACTAGCCAAGAGAGCACCACCATGTAGACGTCCTCGACTCCAAAACTCAGAAGATGTGACCCACACTACACTTCCT TGA-3' (see, e.g., SEQ ID NO: 1).

The underlined sequence in the foregoing SEQ ID NO: 1 is the sequence which is missing in the TAIR annotation after the genome annotation of *Arabidopsis thaliana*. TAIR is now the central agency responsible for assigning *Arabidopsis* locus identifiers (WorldWideWeb at arabidopsis.org). Annotated *Arabidopsis* genes have an AGI-code. AGI stands for *Arabidopsis* Gene Initiative.

SEQ ID NO: 3 is the nucleotide sequence encoding the pre-pro-sequence depicted in SEQ ID NO: 7, which further matures into SEQ ID NO: 8 and finally matures in the plant cell into the mature peptide SEQ ID NO: 4.

The nucleotide sequence (coding sequence) of SEQ ID NO: 3 is depicted in the following sequence: 5'-ATGGCGATGAAGAATACATCACATGTTCTTTTGCTAAGTC TTCTGCTTTGCCTGATGTTTGTGATTGGTCTTGTAGAAGCTAGTATACCAGATGACGA TATGGGTCCAGCAATATATACTCCACCATCAGGATCATGTGGAGCTCCTATTTCCAA ATATGATTTCCAAGTACTAGCCAAGAGACCACCACCATGTAGACGTCCTCGACTCGA AAACACAGAAGATGTGACCCATACTACACGACCTTGA-3' SEQ ID NO: 3 has the AGI code At5g36920.

The open reading frames (ORFs) of At25 and At20 are short (192 and 249 nucleotides, respectively), share 80% coding sequence (CDS) identity and encode peptides of 76 (8.2 kDa) and 82 amino acids (8.9 kDa), respectively.

By "isolated" it is meant material that is substantially or essentially free from components that normally accompany it in its native state. For example, an "isolated polynucleotide," as used herein, refers to a polynucleotide, which has been purified from the sequences which flank it in a naturally-occurring state.

The term "oligonucleotide," as used herein, refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). An oligonucleotide is typically rather short in length, generally from about 10 to 30 nucleotides, but the term can refer to molecules of any length, although the term "polynucleotide" or "nucleic acid" is typically used for large oligonucleotides. The term "polynucleotide" or "nucleic acid," as used herein, designates mRNA, RNA, cRNA, cDNA or DNA. The term typically refers to oligonucleotides greater than 30 nucleotides in length.

The term "recombinant polynucleotide," as used herein, refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "agronomically acceptable carrier" is meant a solid or liquid filler, diluent or encapsulating substance that can be safely used in topical or systemic administration of a peptide of the invention to a plant, plant seed or plant cell.

"Polypeptide," "peptide" and "protein" are used interchangeably herein to refer to a polymer of amino acid residues and to variants and synthetic analogues of the same. Thus, these tennis apply to amino acid polymers in which one or more amino acid residues is a synthetic non-naturally occurring amino acid, such as a chemical analogue of a corresponding naturally occurring amino acid, as well as to naturally-occurring amino acid polymers.

By "recombinant polypeptide" is meant a polypeptide made using recombinant techniques, i.e., through the expression of a recombinant or synthetic polynucleotide. When the chimeric polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The term "sequence identity," as used herein, refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the disclosure, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. "Similarity" refers to the percentage number of amino acids that are identical or constitute conservative substitutions. Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP.

In yet another embodiment, provided is a chimeric gene comprising the following operably linked DNA elements: a) a plant expressible promoter, b) a DNA region encoding for a polypeptide depicted in SEQ ID NO: 5 which upon expression in a plant cell matures into a polypeptide depicted in SEQ ID NO: 2 or a polypeptide which upon expression and maturation in a plant cell is a homologue of SEQ ID NO: 2 with at least 60% identity with SEQ ID NO: 2, and c) a 3' end region comprising transcription termination and polyadenylation signals functioning in cells of a plant.

In the disclosure a "plant expressible promoter" comprises regulatory elements, which mediate the expression of a coding sequence segment in plant cells. For expression in plants, the nucleic acid molecule must be linked operably to or comprise a suitable promoter, which expresses the gene at the right point in time and with the required spatial expression pattern. For the identification of functionally equivalent promoters, the promoter strength and/or expression pattern of a candidate promoter may be analyzed, for example, by operably linking the promoter to a reporter gene and assaying the expression level and pattern of the reporter gene in various tissues of the plant. Suitable well-known reporter genes include, for example, beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of the disclosure). Alternatively, promoter strength may be assayed by quantifying mRNA levels or by comparing mRNA levels of the nucleic acid used in the methods of the disclosure, with mRNA levels of housekeeping genes such as 18S rRNA, using methods known in the art, such as Northern blotting with densitometric analysis of autoradiograms, quantitative real-time PCR or RT-PCR (Heid et al. 1996 Genome Methods 6: 986-994). Generally by "weak promoter" is intended a promoter that drives expression of a coding sequence at a low level. By "low level" is intended at levels of about 1/10,000 transcripts to about 1/100,000 transcripts, to about 1/500,000 transcripts per cell. Conversely, a "strong promoter" drives expression of a coding sequence at high level, or at about 1/10 transcripts to about 1/100 transcripts to about 1/1000 transcripts per cell. Generally, by "medium strength promoter" is intended a promoter that drives expression of a coding sequence at a lower level than a strong promoter, in particular at a level that is in all instances below that obtained when under the control of a 35S CaMV promoter.

The term "operably linked," as used herein, refers to a functional linkage between the promoter sequence and the gene of interest, such that the promoter sequence is able to initiate transcription of the gene of interest.

A "constitutive promoter" refers to a promoter that is transcriptionally active during most, but not necessarily all, phases of growth and development and under most environmental conditions, in at least one cell, tissue or organ. A "ubiquitous" promoter is active in substantially all tissues or cells of an organism. A developmentally-regulated promoter is active during certain developmental stages or in parts of the plant that undergo developmental changes. An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible," i.e., activated when a plant is exposed to various stress conditions, or a "pathogen-inducible" i.e., activated when a plant is exposed to exposure to various pathogens. An organ-specific or tissue-specific promoter is one that is capable of preferentially initiating transcription in certain organs or tissues, such as the leaves, roots, seed tissue, etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific." A seed-specific promoter is transcriptionally active predominantly in seed tissue, but not necessarily exclusively in seed tissue (in cases of leaky expression). The seed-specific promoter may be active during seed development and/or during germination. The seed specific promoter may be endosperm/aleurone/embryo specific. Examples of seed-specific promoters are given in Qing Qu and Takaiwa (Plant Biotechnol. J. 2, 1 13-125, 2004), which disclosure is incorporated by reference herein as if fully set forth. A green tissue-specific promoter as defined herein is a promoter that is transcriptionally active predominantly in green tissue, substantially to the exclusion of any other parts of a plant, whilst still allowing for any leaky expression in these other plant parts.

In a particular embodiment useful promoters of the disclosure can be selected based upon their ability to confer specific expression of a coding sequence (i.e., of an antifungal polypeptide) in response to fungal infection. The infection of plants by fungal pathogens triggers the induction of a wide array of proteins, termed defense-related or pathogenesis-related (PR) proteins (see, for example, Bowles (1990) Ann Rev. Biochem. 59:873-907 and Bol et al. (1990) Ann. Rev. Phytopathol. 28:113-138). Such defense-related or PR genes may encode enzymes involved in phenylpropanoid metabolism (e.g., phenylalanine ammonia lyase, chalcone synthase), proteins that modify plant cell walls (e.g., hydroxyproline-rich glycoproteins, glycine-rich proteins, peroxidases), enzymes that degrade fungal cell walls (e.g., chitinases, glucanases), thaumatin-like proteins, or proteins of as yet unknown function. Defense-related or PR genes have been isolated and characterized from a number of plant species. The promoters of these genes can be used to drive expression of SEQ ID NO: 4, SEQ ID NO: 2 or homologues of at least 70% identity to SEQ ID NO: 2 and biologically functional equivalents thereof in transgenic plants challenged with fungal pathogens. For example, such promoters have been derived from defense-related or PR genes isolated from potato plants (Fritzemeier et al. (1987) Plant Physiol. 85:34-41; Cuypers et al. (1988) Mol. Plant-Microbe Interact. 1:157-160; Logemann et al. (1989) Plant Cell 1:151-158; Matton et al. (1989) Mol. Plant-Microbe Interact. 2:325-331; Schroder et al. (1992) Plant J. 2:161-172). Alternatively, pathogen-inducible promoters such as the PRP1 promoter obtainable from tobacco (Martini et al. (1993) Mol. Gen. Genet. 263: 179) can be employed. Promoters useful in the double-stranded DNA constructs of the disclosure can also be selected based upon their ability to confer specific expression in tissues where the antimicrobial protein is most effective, such as in the flowering parts of the plant. In any case, the particular promoter selected to drive the expression of the antimicrobial proteins of the invention in transgenic plants should be capable of causing sufficient expression of these polypeptide coding sequences to result in the production of an antimicrobial effective amount of the polypeptides in plant tissues. Examples of constitutive promoters capable of driving such expression are the 35S, rice actin, maize ubiquitin, and eIF-4A promoters.

The term "terminator" encompasses a control sequence, which is a DNA sequence at the end of a transcriptional unit, which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

"Selectable marker," "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example, bar which provides resistance to BASTA®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilization of xylose, or antinutritive markers, such as the resistance to 2-deoxyglucose). Expression of visual marker genes results in the formation of color (for example, β-glucuronidase, GUS or β-galactosidase with its colored substrates, for example, X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method. It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can, for example, be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified, for example, by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with $Agrobacteria$, the transformants usually receive only a part of the vector, i.e., the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al. J. Biol. Chem., 275, 2000: 22255-22267; Velmurugan et al. J. Cell Biol., 149, 2000: 553-566). A site-specific integration into the plant genome of the nucleic acid sequences hereof is possible.

For the purposes thereof, "transgenic," "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention. The term "nucleic acid molecule" as used interchangeably with the term "polynucleotide" in accordance with the disclosure, includes DNA, such as cDNA or genomic DNA, and RNA.

A transgenic plant for the purposes hereof is thus understood as meaning, as above, that the nucleic acids used in the method of the invention (e.g., the chimeric genes) are not present in, or originating from, the genome of the plant, or are present in the genome of the plant but not at their natural locus in the genome of the plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e., homologous or, heterologous expression of the nucleic acids takes place. Preferred transgenic plants are mentioned herein.

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

The term "increased expression" or "overexpression," as used herein, means any form of expression that is additional to the original wild-type expression level. For the purposes hereof, the original wild-type expression level might also be zero, i.e., absence of expression or immeasurable expression.

Methods for increasing expression of genes or gene products are well documented in the art and include, for example, overexpression driven by appropriate promoters, as described herein before, the use of transcription enhancers or translation enhancers. Isolated nucleic acids, which serve as promoter or enhancer elements, may be introduced in an appropriate position (typically upstream) of a non-heterologous form of a polynucleotide so as to upregulate expression of a nucleic acid encoding the polypeptide of interest. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell. biol. 8: 4395-4405; Callis et al. (1987) Genes Dev 1:1 183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 1 16, Freeling and Walbot, Eds., Springer, N.Y. (1994).

The term "introduction" or "transformation," as referred to herein, encompass the transfer of an exogenous polynucleotide into a host cell, irrespective of the method used for transfer. Plant tissue capable of subsequent clonal propagation, whether by organogenesis or embryogenesis, may be transformed with a genetic construct of the disclosure and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al. (1982) Nature 296, 72-74; Negrutiu I et al. (1987) Plant Mol Biol 8: 363-373); electroporation of protoplasts (Shillito R. D. et al. (1985) Bio/Technol 3, 1099-1 102); microinjection into plant material (Crossway A et al. (1986) Mol. Gen. Genet. 202: 179-185); DNA or RNA-coated particle bombardment (Klein T M et al. (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP1198985, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. The methods are further described by way of example in B. Jenes et al. Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example, pBin19 (Bevan et al. (1984) *Nucl. Acids Res.* 12-8711). *Agrobacteria* transformed by such a vector can then be used in known manner for the transformation of plants, such as plants used as a model, like *Arabidopsis* or crop plants such as, by way of example, tobacco plants, for example, by immersing bruised leaves or chopped leaves in an agrobacterial solution and then culturing them in suitable media. The transformation of plants by means of *Agrobacterium tumefaciens* is described, for example, by Hofgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with *agrobacteria* and seeds are obtained from the developing plants of which a certain proportion is transformed and thus transgenic [Feldman, K A and Marks M D (1987). Mol Gen Genet. 208:1-9; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). CR Acad Sci Paris Life Sci, 316: 1 194-1 199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition, the stable transformation of plastids is advantageous because plastids are inherited maternally in most crops reducing or eliminating the risk of transgene flow through pollen. The transformation of the chloroplast genome is generally achieved by a process which has been schematically displayed in Klaus et al. 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol. Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al. 2004, Nature Biotechnology 22(2), 225-229).

The genetically modified plant cells can be regenerated via all methods with which the skilled worker is familiar. Suitable methods can be found in the above-mentioned publications by S. D. Kung and R. Wu, Potrykus or Hofgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker, such as the ones described above.

Following DNA transfer and regeneration, putatively transformed plants may also be evaluated, for instance, using Southern analysis, for the presence of the gene of interest, copy number and/or genomic organization. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The term "plant," as used herein, encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods hereof include monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g., *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g., *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g., *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g., *Glycine max, Soja hispida* or *Soja max*), *Gossypium hirsutum, Helianthus* spp. (e.g., *Helianthus annuus*), *Hemerocallis fulva, Hibiscus* spp., *Hordeum* spp. (e.g., *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g., *Lycopersicon* esculentum, Lycopersicon lycopersicum, Lycopersicon pyriforme), Macrotyloma spp., Malus spp., Malpighia emarginata, Mammea americana, Mangifera indica, Manihot spp., Manilkara zapota, Medicago sativa, Melilotus spp., Mentha spp., Miscanthus sinensis, Momordica spp., Moms nigra, Musa spp., Nicotiana spp., Olea spp., Opuntia spp., Ornithopus spp., Oryza spp. (e.g., Oryza sativa, Oryza latifolia), Panicum miliaceum, Panicum virgatum, Passiflora edulis, Pastinaca sativa, Pennisetum sp., Persea spp., Petroselinum crispum, Phalaris arundinacea, Phaseolus spp., Phleum pratense, Phoenix spp., Phragmites australis, Physalis spp., Pinus spp., Pistacia vera, Pisum spp., Poa spp., Populus spp., Prosopis spp., Prunus spp., Psidium spp., Punica granatum, Pyrus communis, Quercus spp., Raphanus sativus, Rheum rhabarbarum, Ribes spp., Ricinus communis, Rubus spp., Saccharum spp., Salix sp., Sambucus spp., Secale cereale, Sesamum spp., Sinapis sp., Solanum spp. (e.g., Solanum tuberosum, Solanum integrifolium or Solanum lycopersicum), Sorghum bicolor, Spinacia spp., Syzygium spp., Tagetes spp., Tamarindus indica, Theobroma cacao, Trifolium spp., Tripsacum dactyloides, Triticosecale rimpaui, Triticum spp. (e.g., Triticum aestivum, Triticum durum, Triticum turgidum, Triticum hybernum, Triticum macha, Triticum sativum, Triticum monococcum or Triticum vulgare), Tropaeolum minus, Tropaeolum majus, Vaccinium spp., Vicia spp., Vigna spp., Viola odorata, Vitis spp., Zea mays, Zizania palustris, Ziziphus spp., amongst others.

The choice of suitable control plants is a routine part of an experimental setup and may include corresponding wild-type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant," as used herein, refers not only to whole plants, but also to plant parts, including seeds and seed parts.

In a particular embodiment, the antimicrobial peptides of the disclosure can be produced synthetically. Chemical synthesis of peptides is well known in the art. Solid phase synthesis is commonly used and various commercial synthesizers are available, for example, automated synthesizers by Applied Biosystems Inc., Foster City, Calif.; Beckman; MultiSyntech, Bochum Germany, GenScript, Jena, etc. Solution phase synthetic methods may also be used, although they are less convenient. For example, peptide synthesis can be carried out using Nα-9-fluorenylmethoxycarbonyl amino acids and a preloaded trityl resin or an aminomethylated polystyrene resin with a p-carboxytritylalcohol linker. Couplings can be performed in dimethylformamide using N-hydroxybenzotriazole and 2-(1H-benzotriazole-1-yl)-1,1,3,3-tetramethyluronium hexafluorophosphate. Commonly used side chain protecting groups are tert-butyl for D, E and Y; trityl for N, Q, S and T; 2,2,4,6,7-pentamethyldihydroxybenzofuran-5-sulfonyl for R; and butyloxycarbonyl for K. After synthesis, the peptides are deprotected and cleaved from the polymer support by treatment with e.g., 92% trifluoracetic acid/4% triethylsilane/4% $H_2O$. The peptides can be precipitated by the addition of tert-butylether/pentane (8:2) and purified by reversed-phase HPLC. The peptides are commonly analyzed by matrix-associated laser desorption time-of-flight mass spectrometry. By using these standard techniques, naturally occurring amino acids may be substituted with unnatural amino acids, particularly D-stereoisomers, and also with amino acids with side chains having different lengths or functionalities. Functional groups for conjugating to small molecules, label moieties, peptides, or proteins may be introduced into the molecule during chemical synthesis. In addition, small molecules and label moieties may be attached during the synthesis process. Preferably, introduction of the functional groups and conjugation to other molecules minimally affect the structure and function of the subject peptide.

In specific embodiments, the N- and C-terminus of the antimicrobial peptides may be derivatized using conventional chemical synthesis methods. The peptides of the invention may contain an acyl group, such as an acetyl group. Methods for acylating, and specifically for acetylating the free amino group at the N-terminus are well known in the art. For the C-terminus, the carboxyl group may be modified by esterification with alcohols or amidated to form-$CONH_2$ or CONHR. Methods of esterification and amidation are well known in the art.

Furthermore, the peptides of the invention may also be produced semi-synthetically, for example, by a combination of recombinant and synthetic production. In the case that fragments of the peptides are produced synthetically, the remaining part of the peptide would have to be produced otherwise, e.g., recombinantly, as described further below, and then be linked to the fragment to form the peptide of the invention. Furthermore, the invention encompasses peptidomimetics of the peptide, as defined above. A peptidomimetic is a small protein- or peptide-like chain designed to mimic a peptide. Peptidomimetics typically arise from modifications of an existing peptide in order to alter the properties of the peptide. For example, they may arise from modifications to change the stability of the peptide. These modifications involve changes to the peptide that will not occur naturally (such as altered backbones and the incorporation of non-natural amino acids), including the replacement of amino acids or peptide bonds by functional analogues. Such functional analogues include all known amino acids other than the 20 gene-encoded amino acids, such as, for example, selenocysteine. The use of peptidomimetics as compared to other mimetics has some particular advantages. For instance, their conformationally restrained structure allows to minimize binding to non-target compounds and to enhance the activity at the desired targets. Through the addition of hydrophobic residues and/or replacement of amide bonds, the transport of peptidomimetics through cellular membranes can be improved. Furthermore, peptidomimetics such as isosters, retro-inverso (all-d retro or retroenantio) peptides and cyclic peptides are less susceptible to degradation by peptidases and other enzymes. Retro-inverso modification of naturally occurring peptides involves the synthetic assemblage of amino acids with α-carbon stereochemistry opposite to that of the corresponding L-amino acids, i.e., D- or D-allo-amino acids, in reverse order with respect to the native peptide sequence. A retro-inverso analogue thus has reversed termini and reversed direction of peptide bonds while approximately maintaining the topology of the side chains as in the native peptide sequence.

In yet another embodiment, provided is a method for recombinant production of an antimicrobial peptide of the disclosure, comprising introducing an expression cassette comprising a nucleic acid encoding an antimicrobial peptide of the invention, introducing the expression cassette in a suitable host cell, culturing the resulting recombinant host under suitable conditions and isolating the antimicrobial peptide produced.

A large number of suitable methods exist in the art to produce peptides in appropriate hosts. If the host is a unicellular organism, such as a prokaryote or a mammalian or insect cell, the person skilled in the art can revert to a variety of culture conditions. Conveniently, the produced protein is harvested from the culture medium, lysates of the cultured cells or from isolated (biological) membranes by established techniques. A preferred method involves the synthesis of nucleic acid sequences by PCR and its insertion into an expression vector. Subsequently, a suitable host cell may be transfected or transformed, etc., with the expression vector. Thereafter, the host cell is cultured to produce the desired peptide, which is isolated and purified.

The term "expression cassette" refers to any recombinant expression system for the purpose of expressing a nucleic acid sequence of the invention in vitro or in vivo, constitutively or inducibly, in any cell, including, in addition to plant cells, prokaryotic, yeast, fungal, insect or mammalian cells. The term includes linear and circular expression systems. The term includes all vectors. The cassettes can remain episomal or integrate into the host cell genome. The expression cassettes can have the ability to self-replicate or not (i.e., drive only transient expression in a cell). The term includes recombinant expression cassettes that contain only the minimum elements needed for transcription of the recombinant nucleic acid.

Appropriate culture media and conditions for the above-described host cells are known in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. $E.\ coli$ can be cultured from 4 to about 37° C., the exact temperature or sequence of temperatures depends on the molecule to be overexpressed. In general, the skilled person is also aware that these conditions may have to be adapted to the needs of the host and the requirements of the peptide or protein expressed. In case an inducible promoter controls the nucleic acid of the invention in the vector present in the host cell, expression of the polypeptide can be induced by addition of an appropriate inducing agent. Suitable expression protocols and strategies are known to the skilled person.

Depending on the cell type and its specific requirements, mammalian cell culture can e.g., be carried out in RPMI or DMEM medium containing 10% (v/v) FCS, 2 mM L-glutamine and 100 U/ml penicillin/streptomycin. The cells can be kept at 37° C. in a 5% $CO_2$, water saturated atmosphere. Suitable media for insect cell culture is e.g., TNM+ 10% FCS or SF900 medium. Insect cells are usually grown at 27° C. as adhesion or suspension culture. Suitable expression protocols for eukaryotic cells are well known to the skilled person and can be retrieved e.g., from Sambrook, 2001.

In a particular embodiment when producing the polypeptides of the disclosure in a host cell, the expression vector may encode a fusion peptide or fusion polypeptide, if the peptide produced exerts toxic activity towards the host cell selected. Furthermore, the vector may encode a fusion peptide or polypeptide, wherein the peptide of the invention is coupled to a signal peptide to direct expression to a specific compartment or site or to a tag which facilitates purification of the fusion peptide or polypeptide. In a specific embodiment, the secretory signal (pre-sequence) and pro-sequence of the antimicrobial polypeptides of the invention are used. The latter means that, for example, to express SEQ ID NO: 2 in a recombinant host, the sequence of SEQ ID NO: 5 is operably linked to a promoter (e.g., a promoter expressed in a host). Alternatively, to express SEQ ID NO: 2 in a recombinant host, the DNA fragment encoding the sequence of SEQ ID NO: 6 is operably linked to a promoter expressed in a host. If the DNA fragment encoding the sequence of SEQ ID NO: 6 is operably linked to a promoter then a (heterologous) pre-peptide encoding sequence should be operably linked to the DNA fragment encoding SEQ ID NO: 6. Alternatively, a DNA fragment encoding SEQ ID NO: 2 is used in combination with a pre- and a pro-sequence encoding nucleotide sequence. Suitable tags are well known in the art and comprise e.g., a hexahistidine tag and a GST (glutathione S-transferase) tag. The fusion peptide or fusion polypeptide expressed has to be processed in order to cleave the compensating but undesired peptide or polypeptide or the signal peptide or tag fused to the peptide of the invention. This can take place at any stage of the purification process after culturing the host cell. Suitable methods to cleave off the undesired part are either chemical methods using e.g., cyanogen bromide, which cleaves at methionine residues or N-chloro succinimide, which cleaves at tryptophan residues. Alternatively, enzymatic methods can be used, which are in general more gentle than chemical methods. Exemplary proteases suitable for cleavage are specific for a certain amino acid sequence and include Factor Xa or TEV protease.

An alternative method for producing the peptide hereof is in vitro translation of mRNA. Suitable cell-free expression systems for use in accordance with the disclosure include rabbit reticulocyte lysate, wheat germ extract, canine pancreatic microsomal membranes, $E.\ coli$ S30 extract, and coupled transcription/translation systems such as the TNT-system (Promega). These systems allow the expression of recombinant peptides or proteins upon the addition of cloning vectors, DNA fragments, or RNA sequences containing coding regions and appropriate promoter elements.

Methods of isolation of the peptide produced are well known in the art and comprise, without limitation, method steps such as ion exchange chromatography, gel filtration chromatography (size exclusion chromatography), affinity chromatography, high pressure liquid chromatography (HPLC), reversed phase HPLC, disc gel electrophoresis or immunoprecipitation (see, for example, Sambrook, 2001).

In a different embodiment, the disclosure relates to a composition comprising a peptide or peptidomimetic of the invention, the nucleic acid molecule of the invention, the vector of the invention or the host cell of the invention.

In a preferred embodiment, the composition is selected from the group consisting of a plant protective composition; and optionally further comprises a suitable carrier and/or diluent.

The term "plant-protective composition" relates to compositions used in the prevention or treatment of diseases related to plants. The term "plant-protective composition" is herein equivalent with the term "plant antimicrobial composition." Formulations of plant-protective compositions comprise wettable powders (WPs) and emulsifiable concentrates (ECs). Being liquids, the EC compositions are easier to handle, their portioning can be handled by a simple volumetric measurement. The biological activity of the EC compositions is usually higher than that of the WP compositions. EC compositions can be prepared only from an active ingredient, which is liquid or, when a solvent can be found in which the active ingredient can be dissolved to give a solution of 10% to 85% concentration (depending on the usual concentrations of the application) without any risk of the interim alteration of the active ingredient. EC compositions usually contain a high amount of solvent. The drawback of the EC compositions can be diminished by formulating the active ingredient in an emulsifiable microemulsion concentrate. Microemulsion is a colloidal system, which in a first approach differs from a true emulsion in the dimension of its particles, which are smaller by an order of magnitude than those of a true emulsion.

According to the general definition, this system contains surface active agents and two immiscible liquids, one of them is usually water, though, in principle, it is also possible to prepare a water-free microemulsion by using another solvent. The surfactant may be the mixture of even 6 to 8 tensides and additionally, it may contain alcohols or amines of medium chain length as auxiliary surfactants (co-surfactants). A "suitable carrier" in connection with the plant protective composition is a non-toxic solid, semisolid or liquid filler, diluent, encapsulating material or formulation auxiliary of any type. Examples of suitable carriers are well known in the art and comprise water or organic solvents as liquids. The suitable composition comprising the peptides of the invention as plant protective composition can be readily determined by the skilled person using methods well known in the art. Non-limiting examples of such methods are the treatment of plants or plant tissues with compositions comprising the peptide of interest and the subsequent infection with bacteria or fungi and analyzing the protective effect of the peptide as compared to control experiments in unprotected plants and plant tissues.

In a specific embodiment, the "plant-protective composition" is a plant antimicrobial composition. In yet another specific embodiment, the antimicrobial composition is an antifungal composition.

The term "antimicrobial activity" in accordance with the disclosure refers to the killing of microorganisms (such as, for example, nematodes, plant pathogenic bacteria or plant pathogenic fungi) or the prevention of the growth of microorganisms by the administration of the peptides hereof to plants, plant cells or plant seeds. The skilled person knows means and methods to determine whether a peptide has an antimicrobial activity. In a specific embodiment, the antimicrobial activity of the peptides of the invention is directed against at least one organism selected from the group of plant bacterial pathogens comprising of *Erwinia carotovora, Erwinia chrysanthemi, Erwinia amylovora, Erwinia stewartii, Ralstonia solanaceaum, Xanthomonas campestris pathovars, Pseudomonas syringae pathovars, Pantoea species, Serratia species, Sphingomonas species, Acidovorax species, Pseudomonas species, Ralstonia species, Rhizobacter species, Rhizomonas species, Xylophilus species, Xylella species, Bacillus species, Clostridium species, Arthrobacter species, Clavibacter species, Curtobacterium species, Leifsonia species, Rhodococcus species, Streptomyces species.*

In a preferred embodiment, the antimicrobial activity of the peptides is directed against at least one organism selected from the group of plant fungal pathogens comprising plant pathogenic *Aspergillus* species, *Penicilium* species, *Alternarias* species (such as *Alternaria brassicicola* and *Alternaria solani*); *Ascochyta* species (such as *Ascochyta pisi*); *Botrytis* species (such as *Botrytis cinerea*); *Cercospora* species (such as *Cercospora kikuchii* and *Cercospora zaea-maydis*); *Colletotrichum* species (such as *Colletotrichum lindemuthianum*); *Diplodia* species (such as *Diplodia maydis*), *Erysiphe* species (such as *Erysiphe graminis* f. sp. *graminis* and *Erysiphe graminis* f. sp. *hordei*); *Fusarium* species (such as *Fusarium nivale, Fusarium oxysporum, Fusarium graminearum, Fusarium culmorum, Fusarium solani, Fusarium moniliforme* and *Fusarium roseum*); *Gaeumanomyces* species (such as *Gaeumanomyces graminis* f. sp. *tritici*); *Helminthosporium* species (such as *Helminthosporium turcicum, Helminthosporium carbonum* and *Helminthosporium maydis*); *Macrophomina* species (such as *Macrophomina phaseolina* and *Maganaporthe grisea*); *Nectria* species (such as *Nectria heamatococca*); *Peronospora* species (such as *Peronospora manshurica* and *Peronospora tabacina*); *Phoma* species (such as *Phoma betae*); *Phymatotrichum* species (such as *Phymatotrichum omnivorum*); *Phytophthora* (such as *Phytophthora cinnamomi* and *Phytophthora cactorum, Phytophthora phaseoli, Phytophthora parasitica, Phytophthora citrophthora, Phytophthora megasperma* f. sp. *sojae* and *Phytophthora infestans*); *Plasmopara* species (such as *Plasmopara uiticola*); *Podosphaera* species (such as *Podosphaera leucotricha*); *Puccinia* species (such as *Puccinia sorghi, Puccinia striiformis, Puccinia graminis* f. sp. *tritici, Puccinia asparagi, Puccinia recondita* and *Puccinia arachidis*); *Puthium* species (such as *Puthium aphanidermatum*); *Pyrenophora* species (such as *Pyrenophora tritici-repentens*); *Pyricularia* species (such as *Pyricularia oryzae*); *Pythium* species (such as *Pythium ultimum*); *Rhizoctonia* species (such as *Rhizoctonia solani* and *Rhizoctonia cerealis*); *Scerotium* species (such as *Scerotium rolfsii*); *Sclerotmia* species (such as *Sclerotinia sclerotiorum*); *Septoria* species (*Septoria lycopersici, Septoria glycines, Septoria nodorum* and *Septoria tritici*); *Thielaviopsis* species (such as *Thielaviopsis basicola*); *Uncinula* species (such as *Uncinula necator*); *Venturia* species (such as *Venturia inaequalis*); and *Verticillium* (*Verticillium dahliae* and *Verticillium alboatrum*).

An antifungal composition, comprising an antifungal effective amount of an isolated polypeptide comprising the amino acid sequence shown in SEQ ID NO: 4 or SEQ ID NO: 2 or a homologue having at least 60%, at least 65%, at least 70% amino acid identity with SEQ ID NO: 2 and an acceptable carrier. The antifungal composition can be used for inhibiting the growth of, or killing of plant pathogenic fungi. These compositions can be formulated by conventional methods known in the art. Necessary formulation aids, such as carriers, inert materials, surfactants, solvents, and other additives are also well known in the art. Using these formulations, it is also possible to prepare mixtures of the present antifungal polypeptide with other pesticidally active substances, fertilizers and/or growth regulators, etc., in the form of finished formulations or tank mixes. In a specific embodiment, antifungal compositions contemplated herein also include those in the form of host cells, such as non-plant pathogenic bacterial and non-plant pathogenic fungal cells, capable of the producing and secreting the present antifungal polypeptide and which can colonize, for example, roots and/or leaves of plants. Examples of non-plant pathogenic bacterial cells that can be used in this manner include strains *Agrobacterium, Arthrobacter, Azospyrillum, Clavibacter, Escherichia, Pseudomonas, Rhizobacterium*, and the like.

Numerous conventional (chemical) fungicides with which the present antifungal polypeptides can be combined are known in the art. These include, for example, polyoxines, nikkomycines, carboxy-amides, aromatic carbohydrates, carboxines, morpholines, inhibitors of sterol biosynthesis, and organophosphorus compounds. Other active ingredients, which can be formulated in combination with the present antifungal polypeptides include, for example, insecticides, attractants, sterilizing agents, acancides, nematocides, and herbicides.

Whether alone or in combination with other active agents, the antifungal polypeptides of the disclosure should be applied at a concentration in the range of from about 0.1 µg/ml to about 100 mg/ml, preferably between about 1 µg/ml and about 5 mg/ml, at a pH in the range of from about 3.0 to about 9.0. Such compositions can be buffered using, for example, phosphate buffers between about 1 mM and 1 M, preferably between about 10 mM and 100 mM, more preferably between about 15 mM and 50 mM. In the case of low buffer concentrations, it is desirable to add a salt to increase the ionic strength, preferably NaCl in the range of from about 1 mM to about 1 M, more preferably about 10 mM to about 100 mM.

In yet another specific embodiment, the chimeric genes encoding the antifungal peptides of the invention can be combined with existing (chimeric) genes encoding antifungal proteins.

In yet another specific embodiment, the antifungal polypeptides of the invention can be applied in combination with existing antifungal polypeptides.

Further scope of the applicability of the disclosure will become apparent from the detailed description and drawings provided below. However, it should be understood that the detailed description and specific examples, while indicating preferred embodiments of the disclosure, are given by way of illustration only since various changes and modifications within the spirit and scope of the invention will become apparent to those skilled in the art from this detailed description. Unless otherwise defined, all technical and scientific terms used herein have the same meaning as commonly understood by one of ordinary skill in the art to which this invention belongs.

EXAMPLES

1. At5g36925 and At5g36920 are Induced During Different Forms of Abiotic Stress

Figure 1:
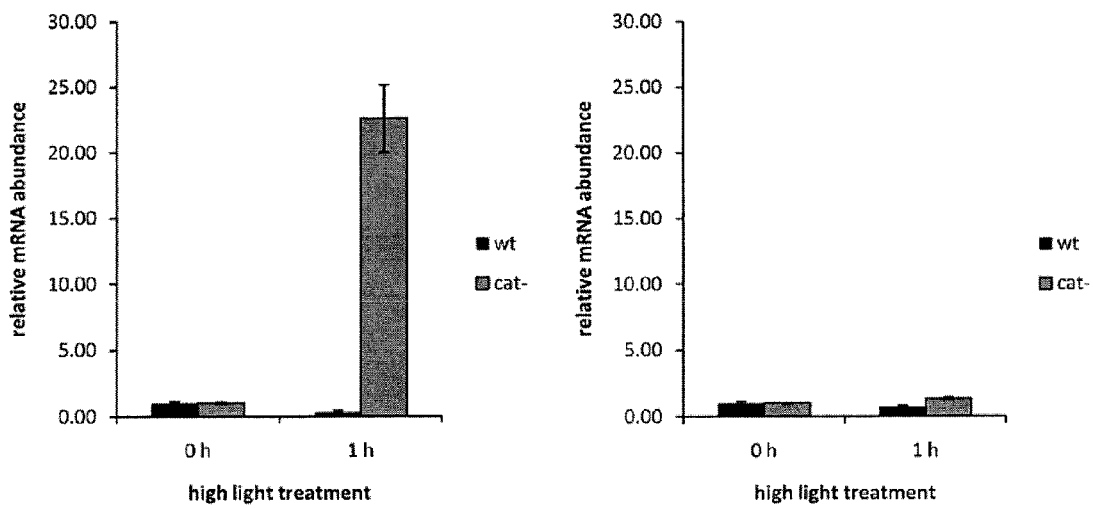
FIG. 1: Transcriptional induction of At5g36925 and At5g36920 towards photorespiratory $H_2O_2$. Previously obtained microarray results (Vanderauwera S. et al. (2011) Proc Natl Acad Sci USA. (4) 1711-6) were verified by quantitative real-time PCR experiments using gene-specific primers (black bars: wild-type, grey bars: catalase-deficient). Transcript abundance is expressed relative to genotype. Data are the means±SE of three technical repeats. (left) At5g36925 is 22-fold induced in catalase-deficient plants after one hour high light treatment. (right) At5g36920 is slightly upregulated in catalase-deficient plants after one hour high light treatment.

During abiotic stress, the metabolic status of the cell is perturbed resulting in the production of a variety of reactive oxygen species (ROS). Besides being toxic byproducts of aerobic metabolism, ROS and, more particularly, $H_2O_2$ are also considered as signaling molecules leading to an elaborate transcriptional response. Previous studies have demonstrated that $H_2O_2$, as a signaling molecule, is involved in a wide variety of processes such as defense and programmed cell death. Both At5g36925 (herein also designated in short as At25) and At5g36920 (herein also designated in short as At20) were identified in a microarray study as being $H_2O_2$-induced genes in catalase-deficient plants subjected to photorespiration-promoting conditions (high light treatment). Quantitative real-time PCR analysis confirmed these microarray results (see FIG. 1). To assess whether At5g36925 and At5g36920 are specific towards a particular stress, we performed quantitative real-time PCR analyses on abiotic stress experiments. Since both At5g36925 and At5g36920 are not present on the ATH1 Affymetrix gene chips, we were restricted on publicly available microarray data, which were generated with Agilent gene chips or Tiling arrays. In the past, the majority of expression analyses were performed with full-length cDNA arrays or oligonucleotide arrays targeting known transcripts. However, these techniques include only transcribed regions determined by expressed sequence tags (EST) or cDNA. Therefore, a vast majority of genes (app. 10 0000 annotated genes) are not included in these analyses; this is also the case for At5g36925 and At5g36920. With the *Arabidopsis thaliana* Tiling Array Express (At-TAX) online resource, it is possible to analyze the effects of high salinity, osmotic, low and high temperature stress as well as the effect of abscisic acid (ABA). In the case of At5g36925, transcripts are only substantially downregulated after a 12 hour treatment of ABA and heat stress. In contrast, the expression profile of At5g36920 shows that it is not differentially regulated by these treatments (data not shown).

Figure 2A:
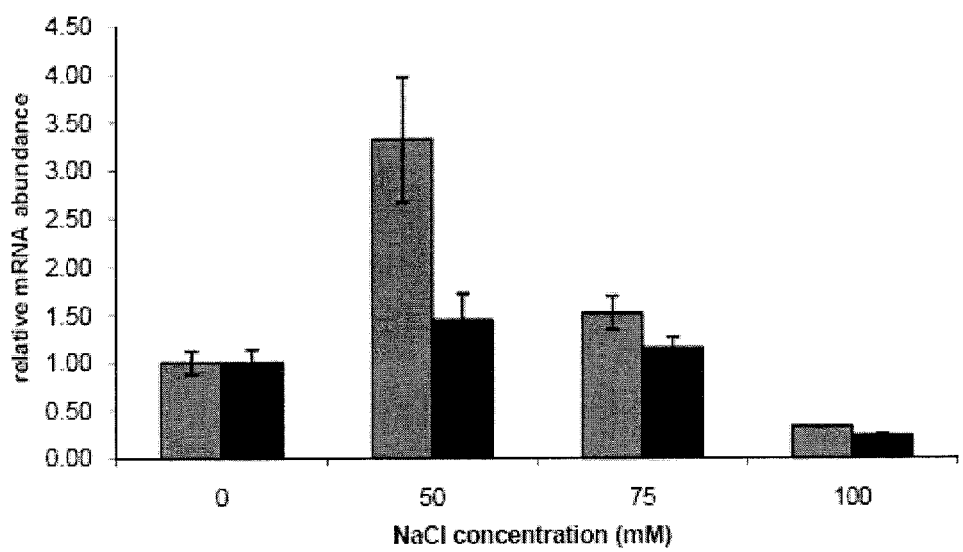
FIG. 2: Expression analysis of At5g36925 and At5g36920 during high salinity, low and high temperature stress. Relative mRNA abundance measured by qRT-PCR is expressed relative to wild-type values and normalized against actin. Data are the means±SE of three biological repeats. At5g36925 is represented by grey bars, At5g36920 by black. (A) At5g36925 is induced during salt stress. Plantlets (stage 1.04) were grown on MS containing 0, 50 mM, 75 mM or 100 mM NaCl and were used for RNA preparation, reverse transcription, and real-time PCR quantification. At5g36925 is approximately 3.5-fold induced when grown on 50 mM NaCl. The expression profile of At5g36920 remains unchanged. (B) Expression profile of At5g36925 and At5g36920 during cold stress. Plants were grown on regular MS till stage 1.04. At5g36925 is shows a clear induction during cold stresses and has the highest induction after 13 hours of incubation at 4° C. At5g36920 is not differentially regulated by cold. (C) Both At5g36920 and At5g36925 show a distinct response towards heat stress. Plants (stage 1.04) were subjected to 0, 1, 6, 12 hours of heat stress (37° C.). At5g36925 is substantially downregulated during heat stress, thereby confirming the tiling-array data. In contrast to At5g36925, At5g36920 is slightly upregulated (2-fold after 12 hours of heat stress).
Figure 2B:
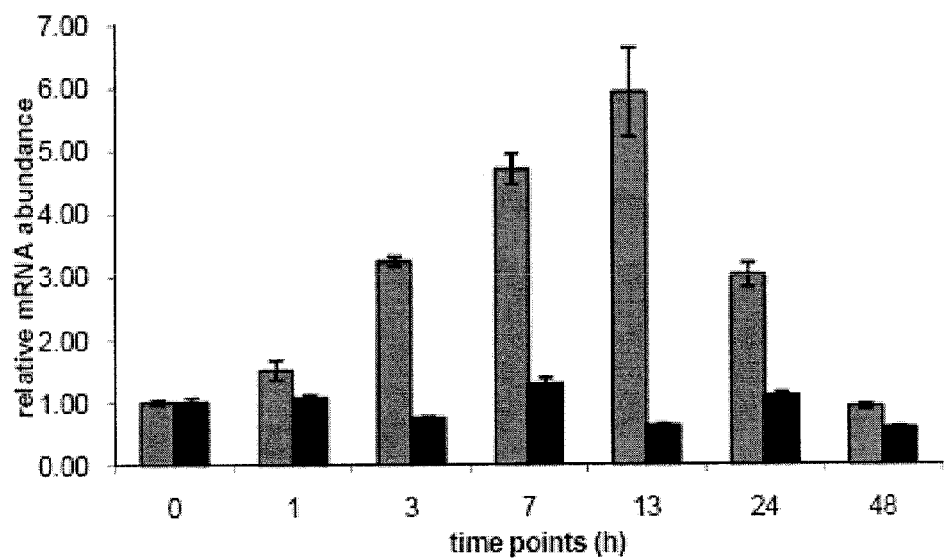
Figure 2C:
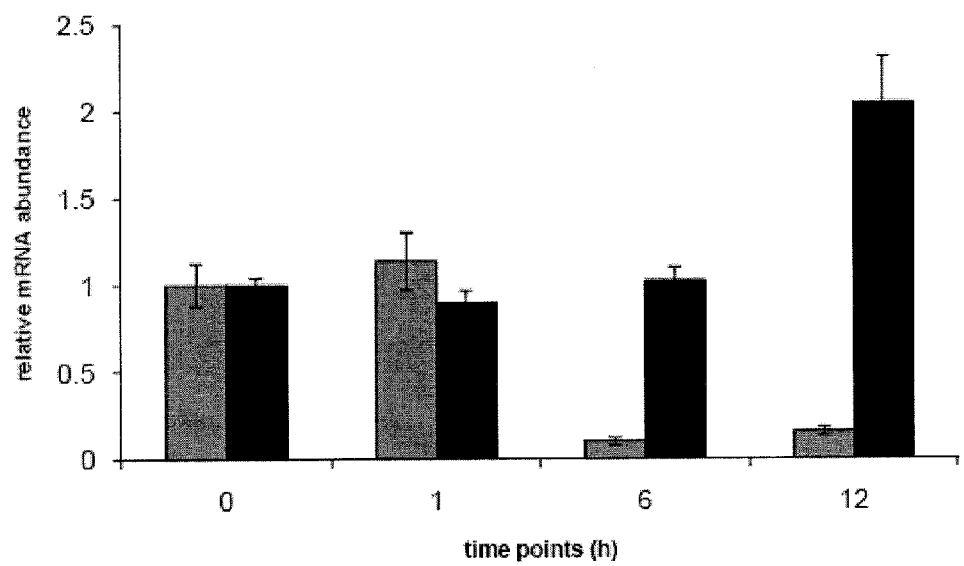

To consolidate these tiling-array data, we performed a detailed expression analysis using quantitative RT-PCR. Therefore, we performed abiotic stress experiments, such as high salinity, low temperature, high temperature and high light stress. Before each abiotic stress treatment, plants were grown till stage 1.04 in vitro under 16 h-light/8 h-dark photoperiods. For the high salinity stress experiment, plantlets were grown till stage 1.04 on medium containing 0, 50, 75, 100 mM NaCl. In the case of the cold and heat stress treatment, plants were transferred to 4° C. and 37° C., respectively. As presented in FIG. 2, transcripts of At5g36925 are transiently upregulated by both high salinity and cold stress, peaking at 50 mM NaCl and 13 hours, respectively. During heat stress, transcripts of At5g36925 are substantially downregulated after 6 and 12 hours. In contrast, At5g36920 is not significantly differentially expressed during these treatments. Probably, this downregulation can be attributed by the fact that most pathogens are not capable of efficiently infecting plant tissues at high temperatures. In conclusion, At5g36925 is responsive towards salt, low and high temperature stress, while the expression of At5g36920 is not affected during these treatments.

2. Tissue-Specific Expression of At25 and At20

To determine in which tissues and specific cell types At25 and At20 are expressed, a promoter:GUS::GFP analysis was carried out. Therefore, the intergenic regions of At25 (1382 bp) and At20 (841 bp) were fused in frame to the reporter gene beta-glucuronidase (GUS) and GFP in the gateway-compatible vector pKGWFS7 (Karimi et al. (2005) Trends in Plant Science 10, 103-105). These reporter constructs were transformed into *Arabidopsis thaliana* ecotype col 0. Remarkably, the expression pattern of At5g36925 and At5g36920 are quite distinct. High expression levels of At20 were detected in young developing leaves, the shoot apical meristem, the hypocotyl, roots and blooming flowers of the adult plant. In leaves, expression was mainly found both in young and mature developed trichomes, in stomatal guard cells, in hydathodes and at the leaf tip. In roots, At5g36920 is highly expressed in lateral root primordia, in emerging lateral roots and in the root tip.

3. At5g36920 and At536925 are Induced Upon *Botrytis cinerea* Infection

To investigate the role of At5g36920 and At5g36925 during biotic stress, we analyzed the response of both genes upon infection with the nectrotrophic fungus *Botrytis cinerea*. Four-week-old *Arabidopsis* plants were inoculated with *Botrytis cinerea* B05-10 and 48 hours post-inoculation both systemic and local leaves were collected. qRT-PCR analysis showed that both genes are significantly induced in systemic leaves. In local leaves, only At5g36920 is induced. These results indicate that not only are both genes regulated by abiotic stress, but also during biotic stress. Interestingly, both genes have opposite gene expression patterns. While At5g36925 shows a distinct response during abiotic stresses, such as salt, cold and heat, it shows only a mild but significant response during pathogen infection. On the contrary, At5g36920, which is highly induced upon *Botrytis* infection (approximately 50-fold induction), is not regulated by abiotic stress.

4. Relationship Between At5g36925 and At5g369204

Figures 3, 4, 5:
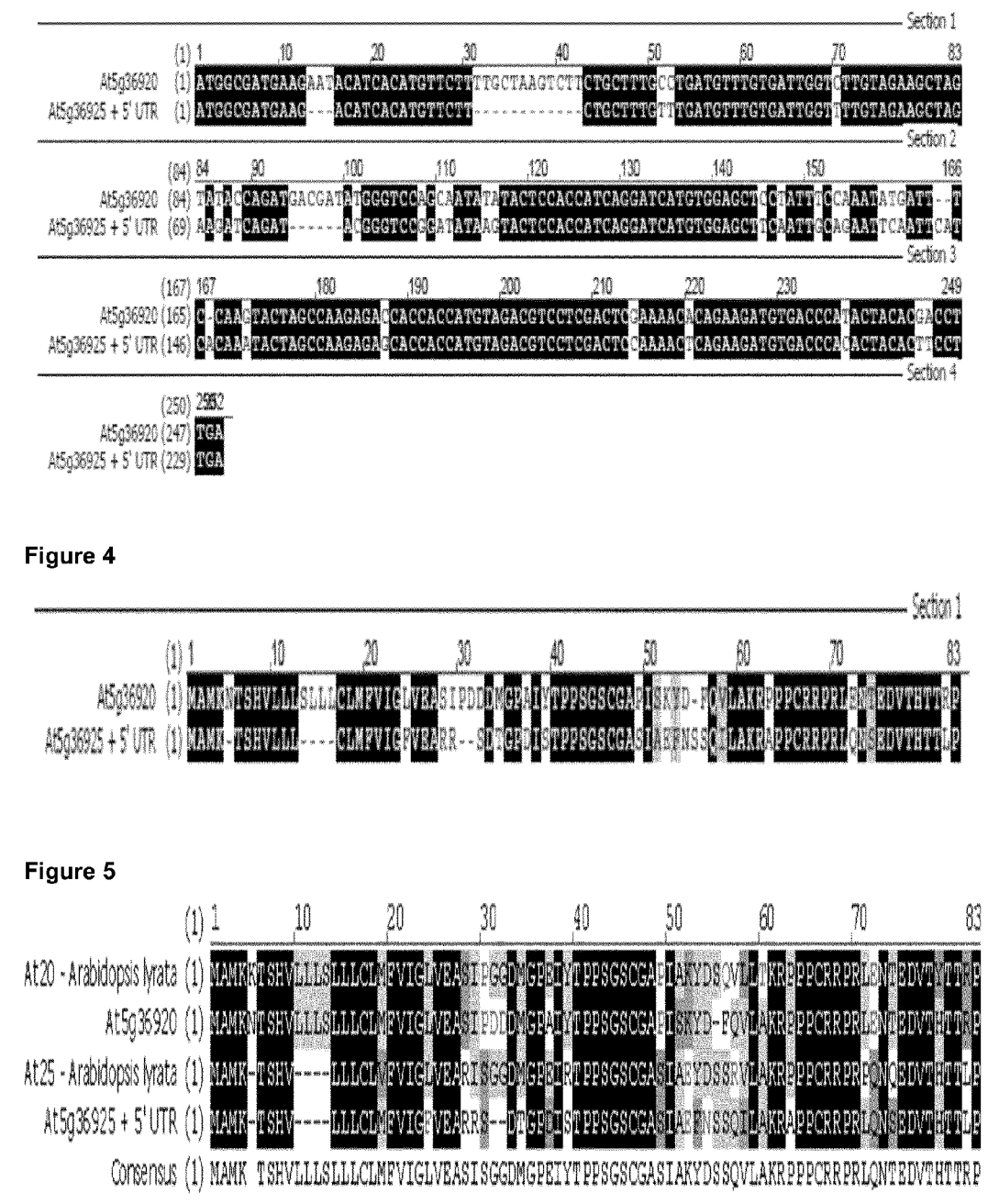

Sequence analysis shows that At5g36925 and At5g36920 are positioned in tandem on the complement strand of chromosome five. Both genes have small open reading frames (ORFs), respectively, 192 and 249 nucleotides. Pair-wise alignment revealed a high degree of similarity between the coding regions of At5g36925 and At5g36920. However, within the upstream region adjacent to the start codon of At5g36925, a sequence was found which was surprisingly similar to the first 54 nucleotides of the coding sequence (CDS) of At5g36920. This upstream sequence contains an AUG codon, which is positioned in frame with the predicted start codon and leads to an open reading frame of 231 nucleotides instead of 192 nucleotides. This 5' positioned AUG codon has an "adequate" Kozak consensus sequence, with a "strong" Kozak sequence being a purine (G) at position –3 or and a G at position +4 and an "adequate" consensus when have only one of these features (see FIGS. 3 and 4).

Since both genes are highly similar and are positioned in tandem, suggesting they are evolved from a recent tandem duplication, we reasoned the annotation of At5g36925 is incorrect. Gene structure annotation of *Arabidopsis thaliana* is performed using different approaches, such as ab initio modeling and annotation using cDNA/EST evidence, which the latter is the case for At5g36925 and At5g36920. Limitations of last mentioned approach mostly result from insufficient cDNA/EST sampling to annotate entire gene structures, which could explain why no EST has been found for this upstream region. To study the evolution of At5g36925 and At5g36920 we used a new on-line comparative genomics tool called PLAZA (Proost S. et al. (2010) The Plant Cell Online 21, 3718-3731). PLAZA 2.0 integrates structural and functional annotation of 23 plants: 11 dicots, 5 monocots, 2 (club-) mosses and 5 algae. Comparative analysis revealed that hitherto only two homologs of At5g36925 and At5g36920 exist and are present in *Arabidopsis lyrata* (A17g33690 and A17g33670, respectively), indicating that these genes are probably *Arabidopsis*-specific. Homologs identified in *Brassica rapa* are depicted in FIG. 10. Interestingly, multiple protein sequence alignment clearly shows that the homolog of At5g36925 contains this additional protein sequence, supporting our analysis that the annotation of At5g36925 is incorrect (see FIG. 5).

In order to determine the exact mRNA length of At5g36925, we performed a 5' rapid amplification of cDNA ends (RACE) using gene-specific primers. As expected, we obtained RACE fragments in which the 5' untranslated leader region (UTR) extends up to 68 nucleotides, whereas according to TAIR the 5'UTR is only 5 nucleotides long. These results strengthen our assumption that this upstream sequence, which is highly similar to At5g36920 functions as a part of the gene.

5. Subcellular Localization of At5g36925 and At5g369205

The subcellular localization of a protein is a key characteristic and can give insights in its function. Therefore, we performed localization experiments in which we transiently expressed green fluorescent protein (GFP) fusions in the epidermal layer of leaves of *N. benthamiana* using agro-infiltration. For At5g36925, the coding region with and without the similar upstream sequence was fused to the GFP reporter and placed under the control of the constitutive cauliflower mosaic virus (CaMV) 35S promoter. In fact, the similar sequence encodes for a hydrophobic region of 19 amino acids, which could lead to the differential targeting of the protein to another compartment of the cell. Indeed, our results suggest that the addition of this similar sequence leads to a completely different subcellular localization of At5g36925. Without this N-terminal sequence, At5g36925 is nucleocytoplasmic, whereas the addition of this sequence leads to the targeting of At5g36925 into the secretory pathway, indicating that this additional sequence contains a functional signal peptide (see FIG. 6). Likewise, the C-terminal fusion of At5g36920 is targeted to the secretory pathway, consistent with in silico predictions. These localizations were confirmed in stable transgenic *Arabidopsis* plants.

6. At5g36920 and At5g36925 are Positioned in Tandem in a Cluster of Defense-Related Genes The spatial genomic organization of a gene can give insights in which process(es) it is involved. Strikingly, both At25 and At20 are flanked by defense-related genes, imposing these genes could be involved in innate immunity (see FIG. 7). Defense genes are often positioned in cluster, which permits a coordinated expression when plant defense is activated. At5g36930, which is positioned upstream of At5g36925, is a disease resistance protein belonging to the TIR-NBS-LRR class. NBS-LRR (nucleotide binding site-leucine rich repeat) resistance genes are part of a large multigene family, which is mainly involved in the detection of pathogens. They also monitor the status of the targets of pathogen virulence effectors, or the cellular consequences of the action of these proteins. At5g36920 is on the other hand flanked by a thionin (Thi2.2, At5g36910). Thionins are small, basic, cysteine-rich antimicrobial peptides, which have a proposed role in plant defense. Currently, about 100 thionin gene sequences were identified in 15 different plant species.

7. At5g36925 and At5g36920 Share Many Characteristics with Antimicrobial Peptides Antimicrobial peptides (AMPs) are small, cationic, secreted peptides, which are widespread throughout the plant kingdom (Theis and Stahl (2004) *Cellular and Molecular Life Sciences* 61, 437-455). They include defensins, thionins, knottins, heveins, snakins and lipid transfer proteins. At5g36925 and At5g36920 have many features in common with AMPs. Both At25 and At20 have an N-terminal signal peptide which targets them to the secretory pathway. The mature peptides are small (~5 kDA), hydrophobic and cationic, which is a key characteristic of antimicrobial peptides. The latter are amphipathic molecules that have clusters of positively charged amino-acid side chains and hydrophobic amino-acid side chains, which allow them to interact with microbial membranes. On the other hand, every reported AMP has a characteristic number and linear arrangement of 6-8 Cys pairs. At25 and At20 both possess only one Cys pair, which presumably forms a disulfide bridge. This could—next to the fact that both genes are not present on the ATH1 array—explain why both peptides were not identified yet as antimicrobial peptides. AMPs have also a defined exon/intron structure. Nearly all AMPs have two exons, of which the first encodes for the signal peptide and the second encodes for the mature peptide (Silverstein K. A. T. et al. (2005) *Plant Physiol.* 138, 600-610). This is also the case for At25 and At20. AMPs are expressed in peripheral cell layers, such as stomata, hydathodes, especially locations where first entry of pathogens take place. Again, both At25 and At20 share this feature of AMPs (see above). Moreover, they are both induced systemically upon *Botrytis* infection and At20 is also highly upregulated in local infected leaves. AMPs are also overrepresented in reproductive tissues (Jones-Rhoades M. W. et al. (2007) *PLoS Genet*, 3, e171). The specific function of AMPs in reproductive organs is still unknown. Since pollen could harbor bacterial and fungal spores, AMPs could protect the female gametophyte during the fertilization phase. During the fertilization process, there is an extensive crosstalk between both the male and the female gametophyte. Interestingly, At25 is expressed in the pollen tube and At20 is expressed in the female gametophyte.

8. Constitutive Overexpression of At20 has a Severe Impact on *Arabidopsis* Growth To assess the impact of constitutive At20 overexpression on symptom development during pathogen infection, we made constitutive overexpression lines using the 35S CaMV promoter. Surprisingly, the overexpression of At20 has a severe impact on normal growth and development of the plant. At20 overexpression seeds germinate normally and have normal cotyledons. Later on, plants are stunted, have curled dark green leaves and the flowering time is severely delayed. It is well known that overexpression of a defense gene can lead to a decrease in fitness-relevant processes such as growth and reproduction. Moreover, constitutive expression of a defense gene often perturbs the expression of other defense-related genes. We, therefore, tested the expression of the salicylic acid responsive marker genes, PR-1 and PR-5, as well as the jasmonic acid responsive marker genes PDF1.2 and both thionins Thi2.1 and Thi2.2. As expected, qRT-PCR showed that overexpression of At20 leads to a distinct response of these marker genes. In all overexpression lines, PDF1.2, PR-1 and PR-5 were substantially upregulated, while Thi2.1 and Thi2.2 were downregulated.

9. Overexpression of At25 Leads to a Decreased Sensitivity Upon *A. brassicicola* and *Botrytis cinerea* Infection To assess the effect of increased At20 or At25 (collectively called ARACINS, respectively, ARACIN2 and ARACIN1) levels on symptom development during fungal infection, we performed disease assays with the two necrotrophic pathogens *A. brassicicola* and *B. cinerea*. Because of the drastic phenotype of the At20$^{OE}$ lines, no accurate scoring of disease symptoms was possible. Therefore, homozygous At25$^{OE}$ plants from three independent transgenic events were assayed with *A. brassicicola* and *B. cinerea* B05-10 by drop inoculation ($5 \times 10^5$ spores mL$^{-1}$) of four-week-old *Arabidopsis* plants. Compared to the wild-type, At25$^{OE}$ lines had an increased resistance phenotype after inoculation with *A. brassicicola*. A drastic reduction of disease symptoms was visible four days after infection: the mean lesion size on leaves of the At25$^{OE}$ overexpression lines was 50% smaller than that on wild-type leaves (see FIG. 8). Moreover, a statistically significant reduction in *Botrytis* lesion size was observed in the At25$^{OE}$ lines (see FIG. 8).

10. In Vitro Antifungal Activity Against *A. brassicola* and *B. cinerea*

Next, we assessed the potential antifungal activity of At25 (ARACIN1) and At20 (ARACIN2) by an in vitro antifungal bioassay. Both propeptide and mature forms of At25 and At20 were produced by chemical synthesis (see Materials and Methods) and tested against *A. brassicicola*, *B. cinerea* B05-10 and *B. cinerea* Korea by means of a microtiter broth dilution assay (FIG. 9). Whereas, proAt25 (also designated as proARACIN1) displayed no statistically significant inhibitory activities (data not shown), the mature form of At25 (also designated as mARACIN1) efficiently inhibited the growth of *A. brassicicola* starting at a concentration of 1 µg mL$^{-1}$, with a 50% growth inhibitory concentration (IC$_{50}$) value of 5.46±0.57 µg mL$^{-1}$. Moreover, the growth of the strains B05-10 and Korea of *B. cinerea* was almost completely inhibited at a concentration of 10 µg mL$^{-1}$ mature At25 (also designated as mARACIN1) (95.7% and 94%, respectively) with IC$_{50}$ values of 3.05±0.25 µg mL$^{-1}$ and 2.03±0.44 µg respectively. In the case of At20 (alos designated as ARACIN2), proAt25 (also designated as proARACIN2) showed a statistically significant antifungal effect starting from 5 µg mL$^{-1}$ (36.7% growth inhibition) against *A. brassicicola* (IC$_{50}$ value 11.32±1.28 µg mL$^{-1}$), and against the *B. cinerea* B05-10 and Korea strains at a higher concentration of 20 µg mL$^{-1}$ (62% and 64.8% growth inhibition, respectively). As expected, the antifungal activity of At20 (ARACIN2) was dramatically increased when the acidic prodomain was not present: the IC$_{50}$ value of mature At20 (mARACIN2) against *A. brassicicola* was significantly lower (1.55±0.11 µg mL$^{-1}$; 86% reduction). Likewise, the antifungal activity of mAt20 (mARACIN2) against *B. cinerea* B05-10 and Korea was remarkably increased in comparison with proAt20 (proARACIN2) (FIG. 9).

11. Generation of Transgenic Corn Plants Expressing At25

Each year, fungal diseases are responsible for extensive agricultural losses. Therefore, the control of plant disease resistance is a prerequisite for the successful utilization of crop species in modern agriculture. Maize (*Zea mays*), together with wheat (*Triticum aestivum*) and rice (*Oryza sativa*) are the three major crop species that account for over 85% of cereal production (FAO Statistical Databases). Enhanced disease resistance through peptide pretreatment or transgenic constitutive expression can have potential use in the field. Therefore, we assess the effect of constitutive expression of At25 in the commercially important crop, corn (*Zea mays*) on disease development by several corn pathogens. Therefore, the At25 CDS is positioned upstream of the constitutive maize ubiquitin promoter. Disease resistance of these constitutive overexpression transgenic lines is assessed against the maize pathogenic fungi *Ustilago maydis*, which causes smut disease and *Fusarium monoliforme*.

Materials and Methods to the Examples Section 1. 5' Rapid Amplification of cDNA Ends (RACE)

*A. thaliana* col 0 plants were grown in vitro (half-strength Murashige and Skoog medium, Ducheva Biochemie, 1% (w/v) sucrose, pH 5.7, with 0.7% (w/v) agar) at 21° C. and under 16-h light/8-h dark photoperiods. Total RNA was extracted using TRIreagens following instructions of the manufacturer (MRC Inc.). 5' RACE-ready cDNA was made using the supplied BD Smart II oligo and BD Powerscript reverse-transcriptase (BD SMART™ RACE cDNA Amplification Kit, BD Biosciences Clontech, Takara Bio USA). The 5' RACE reaction was performed using gene-specific primers (GSP1: TCAAGGAAGTGTAGTGTGGGTCACA TCT (SEQ ID NO: 45), GSP2: CAGGATCATGTGGAGCT-TCAATTGC (SEQ ID NO: 47)) and the supplied universal primer mix. Next, a secondary or "nested" PCR reaction was applied resulting in a single fragment. This 5' RACE fragment was gel-purified using the Nucleospin gel extraction kit (Machinery and Nagel). Afterwards, this fragment was cloned using TOPO cloning into the pENTR/D-TOPO vector (GATEWAY™, Invitrogen, Carlsbad, Calif., USA). The RACE product was identified using sequence-analysis.

2. Fluorescent Protein Fusion Constructs

The open reading frames of At5g36925 and At5g36920 were amplified by RT-PCR and cloned into pDONR221 (Gateway™, Invitrogen, Carlsbad, Calif., USA). Primers were compatible with the GATEWAY™ vector (At5g36925-5UTR-FW, GGGGACAAGTTTGTACAAAAAAGCAG-GCTTCATGGCGATGAAGACATCAC (SEQ ID NO: 14); At5g36925-FW(short), GGGGACAAGTTTGTA-CAAAAAAGCAGGCTCCATGTTTGTGAT-TGGTTTTGTAGAAGC TAG (SEQ ID NO: 15); At5g36925-RV, GGGGACCACTTTGTACAA-GAAAGCTGGGTCTCAAGGAAGTGTAGT-GTGGGTCAC (SEQ ID NO: 16); At5g36925-NS-RV, GGGGACCACTTTGTACAA-GAAAGCTGGGTCAGGAAGTGTAGT-GTGGGTCACATCTT C (SEQ ID NO: 17); At5g36920-FW, GGGGACAAGTTTGTACAAAAAAG-CAGGCTTCATGGCGATGAAGAATACATCAC (SEQ ID NO: 18); At5g36920-RV, GGGGACCACTTTGTACAA-GAAAGCTGGGTCTCAAGGTCGTGTAGTATGGGTC (SEQ ID NO: 19); At5g36920-NS-RV, GGGGACCACTTTGTACAA-GAAAGCTGGGTCAGGTCGTGTAGTATGGGTCAC (SEQ ID NO: 20)). CaMV 35S promoter-driven GFP-fusion constructs were generated in the binary vector pK7FWG2 for C-terminal fusions and pK7WGF2 for N-terminal fusions via LR reactions (GATEWAY™; Karimi et al. (2005) *Trends in Plant Science* 10, 103-105)). Both vectors contain the NPTII kanamycin resistance gene as a selectable marker. The hypervirulent *Agrobacterium* strain LBA4404 was transformed with these constructs and verified by colony PCR using attB1 and attB2 primers.

3. Transient Leaf Blade Transformation

Three week-old *Nicotiana benthamiana* plants grown in strictly controlled conditions (21° C., 18 h light—6 h dark photoperiod) were transiently transformed with *Agrobacterium* by means of syringe infiltration.

4. Confocal Microscopy

Fluorescence microscopy was performed using a confocal microscope 100M with software package LSM 510 version 3.2 (Zeiss, Jena, Germany), equipped with a 63× water corrected objective (numerical aperture 1.2) to scan the leaf epidermis and underlying cell layers. GFP fluorescence was imaged in a single channel setting with 488 nm for GFP excitation.

5. Generation of Overexpression Lines

The open reading frames were amplified by RT-PCR using the high-fidelity Phusion DNA polymerase (Finnzymes O Y, Espoo, Finland) using gene-specific primers flanked by attB1- and attB2 sequences (At5g36925-5UTR-FW, GGG-GACAAGTTTGTACAAAAAA GCAGGCTTCATGGC-GATGAAGACATCAC (SEQ ID NO: 14); At5g36925-FW (short), GGGGACAAGTTTGTA-CAAAAAAGCAGGCTCCATGTTTGTGAT-TGGTTTTGTAGAAGC TAG (SEQ ID NO: 15); At5g36925-RV, GGGGACCACTTTGTACAA-GAAAGCTGGGTCTCAAGGAAGTGTAGT-GTGGGTCAC (SEQ ID NO: 16); At5g36920-FW, GGGGACAAGTTTGTACAAAAAAG-CAGGCTTCATGGCGATGAAGAATACATCAC (SEQ ID NO: 18); At5g36920-RV, GGGGACCACTTTGTACAA-GAAAGCTGGGTCTCAAGGTCGTGTAGTATGGGTC (SEQ ID NO: 19)). The PCR products were cloned into pDONR221 by a BP reaction (GATEWAY™; Invitrogen, Carslbad, Calif., USA). Overexpression constructs were generated using the gateway compatible binary destination pK7WG2 vector (Karimi et al. (2005) *Trends in Plant Science* 10, 103-105). The T-DNA region contains the constitutive CaMV 35S promoter and the NPTII kanamycin resistance selectable marker. The hypervirulent *Agrobacterium* strain LBA4404 was transformed with these constructs and verified with PCR using attB1 and attB2 primers.

6. Generation of Promoter::GUS:GFP Lines

The promoters of At5g36925 (1382 bp; 1343 bp) and At5g36920 (841 bp) were amplified from genomic DNA of *A. thaliana* col 0 wild-type plants using the high-fidelity Phusion DNA polymerase (Finnzymes O Y, Espoo, Finland). Amplification was performed using promoter-specific primers flanked by attB1 and attB2 sequences (PAt5g36925-FW, GGGGACAAGTTTGTACAAAAAAGCAG-GCTTCTAACTTATTTGCAGGGAAC (SEQ ID NO: 9); PAt5g36925-RV, GGGGACCACTTTGTACAA-GAAAGCTGGGTCCAAACAAAGCAGAAGAAC (SEQ ID NO: 10); PAt5g36925-S-RV, GGGGACCACTTTGTACAA-GAAAGCTGGGTCTGGCTCTTCTTATCTCAAG (SEQ ID NO: 11); PAt5g36920-FW, GGGGACAAGTTTGTACAAAAAAG-CAGGCTTCAAACTAGAAATGTTTCAAGAAG (SEQ ID NO: 12); PAt5g36920-RV, GGGGACCACTTTGTACAA-GAAAGCTGGGTCTGGCTCTTCTATCTTAAATAAC (SEQ ID NO: 13)). PCR products were gel-purified using the Nucleospin columns (Machinery and Nagel?). PCR fragment were cloned into the entry vector pDONR221 via a BP reaction and subcloned in the binary destination vector pKGWFS, 0 (Karimi et al. (2005) *Trends in Plant Science* 10, 103-105). The T-DNA region of this vector contains the GUS open reading frame (with intron) in frame with the enhanced GFP gene, which allows promoter analysis both by GUS staining and confocal analysis.

7. Promoter::GUS:GFP Analysis

Whole transgenic seedlings grown in vitro on half-strength MS plates or organs from mature plants grown in soil were harvested and incubated overnight in 90% acetone at 4° C. Acetone was removed and samples were washed with NT-buffer (100 mM Tris, 50 mM NaCl, pH 7.0). Next, the NT-buffer was replaced with ferricyanide solution (0.2 mM ferricyanide, NT-buffer) and samples were incubated in the dark at 37° C. for at least 1 hour. Afterwards, the ferricyanide solution was replaced with GUS staining solution containing 0.02 mM X-gluc (5-bromo-4chloro-3-indolyl-D-glucuronide) in ferricyanide solution. Samples were placed in the dark at 37° C. and incubated for 6 hours or overnight. Afterwards, samples were stored in 100% lactic acid.

8. Plant Materials and Transformation

*A. thaliana* ecotype Col-0 plants were transformed via *Agrobacterium tumefaciens* floral dip (Clough and Bent, 1998). T1 seedlings were grown in vitro on kanamycin-selective medium (half-strength Murashige and Skoog medium, Ducheva Biochemie), 1% (w/v) sucrose, pH 5.7, with 0.7% (w/v) agar at 21° C. and under 16-h light/8-h dark photoperiods. For each construct 10 resistant primary transformed were selected and transferred into soil. GFP-fluorescence of transformants was analyzed using a confocal laser scanning microscope (Zeiss, Jena, Germany).

9. Quantitative Real-Time PCR Experiments

Each abiotic stress experiment was performed using three biological replicates. At each time-point, plant material (rosettes, leaves) was harvested and crushed using liquid nitrogen. RNA was isolated using TRIzol reagens (MRC, Inc.). Two micrograms of total RNA was used as a template to prepare first-strand cDNA using oligo $dT_{15}$-primers and Superscript II (Invitrogen, Carlsbad, Calif., USA). Next, the cDNA samples were diluted 12.5 times of which 5 µL were used as a template. For At5g36925 and At5g36920, gene-specific primers were designed using the Beacon Designer™ software (At5g36925-FW-SyBr, GTAGAAGCTAGAAGAT-CAGATAC (SEQ ID NO: 25); At5g36925-RV-SyBr, TCAAGGAAGTGTAGTGTGG (SEQ ID NO: 26); At5g36920-FW-SyBr, CTAAGTCTTCTGCTTTGCCT-GATG (SEQ ID NO: 27); At5g33920-RV-SyBr, CGTCTA-CATGGTGGTGGTCTC (SEQ ID NO: 28)). Primers were designed using the Universal PROBELIBRARY® Assay Design center ProbeFinder software (on the World Wide web at roche-applied-science.com/, Roche) for the following genes: PR-1_At2g14610-PL-FW, TGATCCTCGTGG-GAATTATGT (SEQ ID NO: 35); PR-1_At2g14610-PL-RV, TGCATGATCACATCATTACTTCAT (SEQ ID NO: 36); PR-5_At1g75040-PL-FW, GACTGTGGCGGTCTAA-GATGT (SEQ ID NO: 37); PR-5_At1g75040-PL-RV, TGAATTCAGCCAGAGTGACG (SEQ ID NO: 38); Thi2-1_At1g72260-PL-FW, CTGGTCATGGCACAAGTTCA (SEQ ID NO: 39); Thi2-1_At1g72260-PL-RV, GCCATTTCTAGCTTGGTTGG (SEQ ID NO: 40); Thi2-2_At5g36910-PL-FW, TGACCACTCTC-CAAAACTTTGAC (SEQ ID NO: 41); Thi2-2_At5g36910-PL-RV, CTTTTAACTGCGGCGGTAGA (SEQ ID NO: 42); Pdf1-2_At5g44420-PL-FW, GTTCTCTTTGCTGCTTTC-GAC (SEQ ID NO: 43); Pdf1-2_At5g44420-PL-RV, GCAAACCCCTGACCATGT (SEQ ID NO: 44). Real-time PCR was performed on an iCycler (bio-Rad, Hercules, Calif.) using 200 nM primers and Platinum Sybr green Supermix-UGD (2×) (Invitrogen, Carlsbad, Calif.), supplemented with fluorescein dye in a final volume of 25 uL per reaction, following manufacturer's instructions. All reactions were performed in triplicate. Actin-related protein 7 (At3g60830) was used as a reference gene.

10. Disease Assays

*Arabidopsis thaliana* mutant and Col-0 (wild-type) plants were grown in untreated soil ("Zaai-en stekgrond," DCM, Sint-Katelijne-Waver, Belgium) in a growth chamber with 21° C. daytime temperature, 18° C. night-time temperature, 75% humidity and a 12 h day-light cycle with a light intensity of approximately 120 μ/mol/m²s. Four weeks old plants were inoculated with *Botrytis cinerea* B05-10. To this end, a $2 \times 10^7$ spores/ml solution of *B. cinerea* was diluted in ½ PDB (12 g/l Potato Dextrose Broth in water) to a final concentration of $5 \times 10^5$ spores/ml. After spotting 5 μl of this dilution on two leaves/plant, the plants were placed in a humid chamber. Disease symptoms were scored by measuring the average diameters of the necrotic lesions on various days after *B. cinerea* inoculation. This disease assay was repeated twice with an average of 220 plants/assay. For each assay, the average lesion diameter of wt and mutant plants were compared using a t-test.

11. Antifungal Activity Assay

Synthetic proAt25 peptide, mature At25 peptide, proat20 and mature At20 peptides were purchased from genscript (on the World Wide web at genscript.com). Stock solutions of $2 \times 10^7$ spores/ml of *Botrytis cinerea* B05-10, *Botrytis cinerea* Korea, *Fusarium oxysporum* and *Alternaria brassicicola* were diluted in ½ PDB (12 g/l Potato Dextrose Broth in water) to a final concentration of $2 \times 10^4$ spores/ml. After adding 196 μl aliquots of these spore dilutions to 4 μl of 2-fold dilution series of At25 in DMSO (starting from a 100 μg/ml stock solution) in microtiter plates, the plates were incubated on 23° C. for 48 h. DMSO was used as a negative control. Growth of the fungi was evaluated both microscopically and by measuring the $OD_{600}$. Each fungus was tested in duplicate in the microtiter plates. Additionally, for *Alternaria brassicicola* this antifungal assay was repeated twice. For each assay, the average $OD_{600}$ of each dilution and the DMSO control were compared using a t-test.

12. Sequences of the primers

| primer | sequence | SEQ ID NO: |
|---|---|---|
| promoter cloning | | |
| PAt5g36925-FW | GGGGACAAGTTTGTACAAAAAAGCAGGCTTCTAACTTATTTGCAGGGAAC | 9 |
| PAt5g36925-RV | GGGGACCACTTTGTACAAGAAAGCTGGGTCCAAACAAAGCAGAAGAAC | 10 |
| PAt5g36925-S-RV | GGGGACCACTTTGTACAAGAAAGCTGGGTCTGGCTCTTCTTATCTCAAG | 11 |
| PAt5g36920-FW | GGGGACAAGTTTGTACAAAAAAGCAGGCTTCAAACTAGAAATGTTTCAAGAAG | 12 |
| PAt5g36920-RV | GGGGACCACTTTGTACAAGAAAGCTGGGTCTGGCTCTTCTATCTTAAATAAC | 13 |
| CDS cloning | | |
| At5g36925-5UTR-FW | GGGGACAAGTTTGTACAAAAAAGCAGGCTTCATGGCGATGAAGACATCAC | 14 |
| At5g36925-FW (short) | GGGGACAAGTTTGTACAAAAAAGCAGGCTCCATGTTTGTGATTGGTTTTGTAGAAGCTAG | 15 |
| At5g36925-RV | GGGGACCACTTTGTACAAGAAAGCTGGGTCTCAAGGAAGTGTAGTGTGGGTCAC | 16 |
| At5g36925-NS-RV | GGGGACCACTTTGTACAAGAAAGCTGGGTCAGGAAGTGTAGTGTGGGTCACATCTTC | 17 |

12. Sequences of the primers

| primer | sequence | SEQ ID NO: |
|---|---|---|
| At5g36920-FW | GGGGACAAGTTTGTACAAAAAAGCAGGCTTCATGGCGATGAAGAATACATCAC | 18 |
| At5g36920-RV | GGGGACCACTTTGTACAAGAAAGCTGGGTCTCAAGGTCGTGTAGTATGGGTC | 19 |
| At5g36920-NS-RV | GGGGACCACTTTGTACAAGAAAGCTGGGTCAGGTCGTGTAGTATGGGTCAC | 20 |
| amiRNA cloning | | |
| I-miR-s | GATAGGACGTCTACATGGTGGTCTCTCTCTTTTGTATTCC | 21 |
| II-miR-a | GAGACCACCATGTAGACGTCCTATCAAAGAGAATCAATGA | 22 |
| III-miRCs | GAGAACACCATGTAGTCGTCCTTTCACAGGTCGTGATATG | 23 |
| IV-miRCa | GAAAGGACGACTACATGGTGTTCTCTACATATATATTCCT | 24 |
| Sybr green qRT-PCR | | |
| At5g36925-FW-SyBr | GTAGAAGCTAGAAGATCAGATAC | 25 |
| At5g36925-RV-SyBr | TCAAGGAAGTGTAGTGTGG | 26 |
| At5g36920-FW-SyBr | CTAAGTCTTCTGCTTTGCCTGATG | 27 |
| At5g33920-RV-SyBr | CGTCTACATGGTGGTGGTCTC | 28 |
| SALK genomic PCR | | |
| SALK_LBb1_3 | ATTTTGCCGATTTCGGAAC | 29 |
| SALK_LBa1 | TGGTTCACGTAGTGGGCCATCG | 30 |
| SALK_054075_LP | TCCACATGTCATCACCTTCTC | 31 |
| SALK_054075_RP | GAGTCGAGGACGTCTACATGG | 32 |
| SALK_062537_LP | AGACGATTTCACATTGCCATC | 33 |
| SALK_062537_RP | AGATAAGAAGAGCCAATGGCG | 34 |
| PROBELIBRARY ® qRT-PCR | | |
| PR-1_At2g14610-PL-FW | TGATCCTCGTGGGAATTATGT | 35 |
| PR-1_At2g14610-PL-RV | TGCATGATCACATCATTACTTCAT | 36 |
| PR-5_At1g75040-PL-FW | GACTGTGGCGGTCTAAGATGT | 37 |
| PR-5_At1g75040-PL-RV | TGAATTCAGCCAGAGTGACG | 38 |
| Thi2-1_At1g72260-PL-FW | CTGGTCATGGCACAAGTTCA | 39 |
| Thi2-1_At1g72260-PL-RV | GCCATTTCTAGCTTGGTTGG | 40 |
| Thi2-2_At5g36910-PL-FW | TGACCACTCTCCAAAACTTTGAC | 41 |
| Thi2-2_At5g36910-PL-RV | CTTTTAACTGCGGCGGTAGA | 42 |

| 12. Sequences of the primers | | |
|---|---|---|
| primer | sequence | SEQ ID NO: |
| Pdf1-2_At5g44420-PL-FW | GTTCTCTTTGCTGCTTTCGAC | 43 |
| Pdf1-2_At5g44420-PL-RV | GCAAACCCCTGACCATGT | 44 |
| 5' RACE | | |
| At25-GSP1 | TCAAGGAAGTGTAGTGTGGGTCACATCT | 45 |
| At25-NGSP1 | TCTGAGTTTTGGAGTCGAGGACGTC | 46 |
| At25-GSP2 | CAGGATCATGTGGAGCTTCAATTGC | 47 |
| At25-NGSP2 | CAATTCATCACAAATACTAGCCAAGAGAGC | 48 |
| NUP-TOPO | CACCAAGCAGTGGTATCAACGCAGAGT | 49 |

The invention claimed is:

1. A chimeric gene comprising the following operably linked DNA elements:
   a) a plant expressible promoter,
   b) a DNA region encoding a polypeptide selected from the group consisting of SEQ ID NO:4, SEQ ID NO:2, and a homologue of SEQ ID NO:2 having at least 95% sequence identity to SEQ ID NO:2, wherein the polypeptide has antifungal activity, and
   c) a 3' end region comprising transcription termination and polyadenylation signals functioning in cells of a plant,
   wherein the plant expressible promoter is heterologous to the DNA region.

2. A transgenic plant or a transgenic seed or a transgenic plant cell comprising a chimeric gene comprising the following operably linked DNA elements:
   a plant expressible promoter,
   DNA encoding a peptide selected from the group consisting of SEQ ID NO:4, SEQ ID NO:2, and a homologue of SEQ ID NO:2 having at least 95% sequence identity to SEQ ID NO:2, wherein the peptide confers resistance to the transgenic plant, seed, or cell to *Alternaria brassicicola* and *Botrytis cinerea*, and
   a 3' end region comprising transcription termination and polyadenylation signals functioning in cells of a plant.

3. A method for controlling microbial damage to a plant, the method comprising:
   introducing into the genome of a plant the chimeric gene comprising the following operably linked DNA elements:
   a plant expressible promoter,
   DNA region encoding a peptide selected from the group consisting of SEQ ID NO:4, SEQ ID NO:2, and a homologue of SEQ ID NO:2 having at least 95% sequence identity to SEQ ID NO:2, and
   a 3' end region comprising transcription termination and polyadenylation signals functioning in cells of a plant.

4. The method according to claim 3, wherein said microbial damage is fungal damage.

5. A polynucleotide comprising the following operably linked DNA elements:
   a plant expressible promoter, operably linked to
   a DNA region encoding a polypeptide selected from the group consisting of SEQ ID NO:4, SEQ ID NO:2, and a homologue of SEQ ID NO:2 having at least 95% sequence identity to SEQ ID NO:2, wherein the polypeptide has antifungal activity, and
   a 3' end region comprising transcription termination and polyadenylation signals functioning in cells of a plant,
   wherein the promoter is heterologous to the DNA region.

6. A transgenic plant cell comprising a polynucleotide comprising the following operably linked DNA elements:
   a plant expressible promoter,
   DNA encoding a peptide selected from the group consisting of SEQ ID NO:4, SEQ ID NO:2, and a homologue of SEQ ID NO:2 having at least 95% sequence identity to SEQ ID NO:2 wherein the peptide confers resistance to the transgenic plant cell to *Alternaria brassicicola* and *Botrytis cinerea*, and a 3' end region comprising transcription termination and polyadenylation signals functioning in cells of a plant, wherein the plant expressible promoter is heterologous to the DNA.

7. The chimeric gene of claim 1, wherein the DNA region encodes SEQ ID NO:4.

8. The chimeric gene of claim 1, wherein the DNA region encodes SEQ ID NO: 2.

9. The transgenic plant, transgenic seed, or transgenic plant cell of claim 2, wherein the DNA encodes SEQ ID NO:4.

10. The transgenic plant, transgenic seed, or transgenic plant cell of claim 2, wherein the DNA encodes SEQ ID NO:2.

11. The method according to claim 3, wherein the DNA region encodes SEQ ID NO:4.

12. The method according to claim 3, wherein the DNA region encodes SEQ ID NO:4.

13. The polynucleotide of claim 5, wherein the DNA region encodes SEQ ID NO:4.

14. The polynucleotide of claim 5, wherein the DNA region encodes SEQ ID NO:2.

15. The transgenic plant cell of claim 6, wherein the DNA encodes SEQ ID NO:4.

16. The transgenic plant cell of claim 6, wherein the DNA encodes SEQ ID NO:2.

* * * * *